United States Patent
Okada et al.

(10) Patent No.: US 7,858,610 B2
(45) Date of Patent: Dec. 28, 2010

(54) PREVENTIVE AND/OR REMEDY FOR LOWER URINARY TRACT DISEASES CONTAINING $EP_4$ AGONIST

(75) Inventors: Hiroki Okada, Mishima-gun (JP); Takayuki Maruyama, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 11/660,043

(22) PCT Filed: Aug. 9, 2005

(86) PCT No.: PCT/JP2005/014875
§ 371 (c)(1),
(2), (4) Date: Feb. 12, 2007

(87) PCT Pub. No.: WO2006/016689
PCT Pub. Date: Feb. 16, 2006

(65) Prior Publication Data
US 2008/0021021 A1    Jan. 24, 2008

(30) Foreign Application Priority Data
Aug. 10, 2004    (JP) ............... 2004-232985

(51) Int. Cl.
*A61K 31/54* (2006.01)
*A61K 31/535* (2006.01)
(52) U.S. Cl. ............... 514/183; 514/227.5; 514/228.8; 514/238.8
(58) Field of Classification Search ............ None
See application file for complete search history.

(56) References Cited

U.S. PATENT DOCUMENTS

| | | | |
|---|---|---|---|
| 6,462,081 B1 | 10/2002 | Maruyama et al. | |
| 6,835,752 B2 | 12/2004 | Tani et al. | |
| 2003/0216381 A1 | 11/2003 | Tani et al. | |
| 2004/0235825 A1 | 11/2004 | Tani et al. | |
| 2005/0020686 A1 | 1/2005 | Maruyama et al. | |
| 2005/0026908 A1 | 2/2005 | Tani et al. | |
| 2006/0100195 A1 | 5/2006 | Maruyama et al. | |
| 2006/0258728 A1 | 11/2006 | Tani et al. | |

FOREIGN PATENT DOCUMENTS

| | | |
|---|---|---|
| WO | 00/03980 A1 | 1/2000 |
| WO | 02/16311 A1 | 2/2002 |
| WO | 03/009872 A1 | 2/2003 |
| WO | 03/016254 A1 | 2/2003 |
| WO | 03/043655 A1 | 5/2003 |

OTHER PUBLICATIONS

Hurst. Identification of proteoglycans present at high density on bovine and human bladder luminal surface. World J Urol, 12(1):3-10, 1994.*
Takahashi et al. EP4 receptor mediation of prostaglandin E2-stimulated mucus secretion by rabbit gastric epithelial cells. Biochem Pharmacol 58:1997-2002, 1999.*
Maruyama et al (Bioorg Med Chem 10:1743-1759, 2002).*
Kelly et al (Eur Urol 34:53-56, 1998).*
Dell and Parsons (J Reprod Med 49:243-252, 2004).*
Li et al (Neurosci Lett 438:210-215, 2008).*
Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Stella et al (Prodrugs: Challenges and Rewards, Part 1, 2007).*
Fossaluzza et al.; "Misoprostol-induced Urinary Incontinence"; Journal of Internal Medicine; No. 230: pp. 463-464; 1991.

* cited by examiner

*Primary Examiner*—Brandon J Fetterolf
*Assistant Examiner*—Craig Ricci
(74) *Attorney, Agent, or Firm*—Sughrue Mion, PLLC

(57) ABSTRACT

(1) A preventive and/or a remedy for lower urinary tract diseases such as inflammation in the lower urinary tract, cystitis (interstitial cystitis, etc.) and urethritis; (2) an agent for improving bladder compliance and/or bladder capacity; and (3) an agent for protecting bladder mucosa and/or bladder epithelial cells and/or promoting the regeneration thereof; each containing an $EP_4$ agonist.

An $EP_4$ agonist is useful in ameliorating symptoms of lower urinary tract diseases such as (1) frequent urination, (2) urgency of urination, (3) pain in the reproductive organs and/or lower urinary tract (for example, bladder pain, urinary tract pain, vulvar pain, vaginal pain, scrotal pain, perineal pain, pelvic pain, etc.) and/or (4) discomfort in the reproductive organs and/or lower urinary tract. Among all, a selective $EP_4$ agonist is useful as a preventive and/or remedy for lower urinary tract diseases having no side effect.

1 Claim, 2 Drawing Sheets

PREVENTIVE AND/OR REMEDY FOR LOWER URINARY TRACT DISEASES CONTAINING EP$_4$ AGONIST

This is a national stage application under 35 U.S.C. 371 of PCT/JP2005/014875 filed on Aug. 9, 2005, which claims priority to Japanese patent application 2004/232985 filed on Aug. 10, 2004, all of which are incorporated herein by reference.

TECHNICAL FIELD

The present invention relates to (1) a preventive and/or treatment agent for lower urinary tract diseases; (2) an agent for improving bladder compliance and/or bladder capacity; and (3) an agent for protecting bladder mucosa and/or bladder epithelial cells and/or promoting the regeneration thereof, each comprising an EP$_4$ agonist which is used as medicament.

BACKGROUND ART

Lower urinary tract diseases are the state where disorder exists in any of the bladder and excretory path thereof, which is recognized and diagnosed as lower urinary tract symptoms. The lower urinary tract symptoms are classified into urination symptom, post-urination symptom, pooled urine symptom, pain in reproductive organs and/or lower urinary tract, etc. Urination symptom is appeared during an urination phase and is a symptom such as reduced urinary stream, divided urinary stream, stopped urinary stream, retarded urination, urination by abdominal pressure and terminal dropping. Post-urination symptom is a symptom which is appeared immediately after urination such as sensation of residual urine and urine dropping after urination. Pooled urine symptom is appeared during a pooled urine phase and is a symptom such as pollakiuria during daytime, pollakiuria during the night, urgency of urination, urinary incontinence and exaltation or lowering of bladder sense. Examples of pain in reproductive organs and/or lower urinary tract are bladder pain, urinary tract pain, vulvar pain, vaginal pain, scrotal pain, perineal pain, pelvic pain.

Causes for lower urinary symptoms include (1) disorder of nerve governing the bladder and/or the urethral sphincter caused by spinal damage, cerebrospinal tumor, cerebrospinal blood vessel disorder, myelitis, multiple sclerosis, Parkinson's disease, myelomeningocele, radical operation for uterine cancer, radical operation for rectal cancer, etc.; (2) stimulation to bladder mucosa, inflammation or fibrosis of bladder muscle layer by lesion of bladder wall such as cystitis, prostatitis, calculus at the lower end of the urinary tract and bladder cancer; (3) injury of urethral sphincter; and (4) presence of obstructive lesion of the urinary tract by prostatic hyperplasia, prostatic cancer, bladder neck sclerosis, urethral stricture, etc. In the treatment therefor, treatment of causing diseases therefor is fundamental. When the treatment cannot be carried out, symptomatic treatment is carried out.

Among the lower urinary tract diseases, cystitis means infectious or non-infectious inflammation mostly in bladder mucosa and tissues under the mucosa. Sometimes, it is extended to muscular coat. By its clinical course, it is usually classified into acute cystitis and chronic cystitis. By the presence or absence of obstructive diseases of lower the urinary tract, it is classified into simple cystitis and complexity cystitis. Generally, there are many cases where simple cystitis proceeds acutely and well reacts to antibacterial agents while complexity cystitis proceeds chronically and hardly reacts to antibacterial agents whereby it is sometimes called intractable cystitis. When the cause cannot be identified in intractable cystitis, the cystitis is called primary interstitial cystitis while interstitial cystitis, bacterial intractable cystitis, hemorrhagic cystitis, eosinophilic cystitis, etc. which is caused by the following (1) to (5) are called secondary interstitial cystitis. Thus, (1) infectious diseases of the bladder, the urethra, the prostate gland and the vagina; (2) cystitis by tuberculosis or *bacillus* Calmette-Guerin (hereinafter, it may be referred to as BCG); (3) drug-induced cystitis by, such as, cyclophosphamide; (4) radiation cystitis; and (5) cancer of the bladder, the uterus, the vagina and the urethra (refer to Iyaku Journal, volume 31, no. 3, page 81, published in 1995; Hainyo Shogai Practice, volume 12, no. 1, page 36, published in 2004).

With regard to the bacterial intractable cystitis, bladder tuberculosis is a representative one. Bladder tuberculosis shows strong cystitis syndrome and pyuria. Common antibacterial agents are ineffective therefor. Hemorrhagic cystitis is cystitis where strong hematuria is a chief complaint. There are various causes therefor and it is not a single disease. Main causes are (1) virus such as adenovirus and influenza virus; (2) bacteria such as *Escherichia coli*, proteus and *Pseudomonas aeruginosa* and other microorganisms; and (3) physical and/or chemical stimulation(s) such as irradiation of radioactive ray and administration of agents (e.g., cyclophosphamide, hexamine mandelate and methicillin). There were some cases which were believed to be allergic. However, usually, it is not easy to prove to be surely allergic. Additionally, frequency thereof is not clear as well. Although eosinophilic cystitis shows the same symptom and pyuria as in the case of acute bacterial cystitis, urine culture is negative and antibacterial agents are ineffective. Its pathology is an allergic reaction to agents having an anti-allergic activity. Although tranilast is representative, other anti-allergic agents may also cause the same cystitis. From a pathological view, chief ones are chronic inflammation observations without characteristics. Although there are many cases which are easily recovered by ceasing the administration of the causing agents, it is sometimes necessary to administer steroid or, further, extract the bladder if recovery is hardly achieved.

Primary interstitial cystitis is positioned as a chronic inflammatory disease of bladder interstitial tissue where cause is ambiguous without urinary infection or specific pathological observation in which chief symptoms are urine accumulation symptom such as strong pollakiuria (e.g., there are some cases where about 6 to 70 urinations a day are necessary) and urinary urgency, and pain and unpleasant sensation of generative organs and/or lower the urinary tract in urine accumulation, urination and post-urination. In 1987, although NIH (National Institute of Health) of the United States issued diagnostic criteria for the studies of primary interstitial cystitis, they have been said to be still insufficient. Additionally, in the United States, although it has been said that there are as many as about 700,000 patients and 90% thereof are female, little is known about this diseases. It has been said that the causes for this disease include such as lymphatic disorder, chronic infectious disease, neural disorder, mental disorder, autoimmune disease, vasculitis, toxic factor in urine and destruction of defensive function of the bladder and mast cell. However, the real causes have not been made clear yet (*Rinsho Hinyokika*, volume 52, no. 9, page 635, published in 1998). Among them, injury of glycosaminoglycan (hereinafter, abbreviated as GAG) is believed to be an important factor. Permeation of bladder mucosa is enhanced by deficiency of GAG, and not only potassium but also normal substances in urine are permeated through the mucosa to stimulate C-fiber in sensory nerve and activate mast cells. It has been believed that such a cascade is induced one after another to occur the symptom. At present, a method for treating this primary interstitial cystitis includes the method which is not for complete recovery but a mere symptomatic treatment. Methods such as a hydraulic expansion method where the bladder which is fibrosed and contracted is mechanically expanded and an intravesical injection therapy of heparin preparation, dimethyl sulfoxide preparation, hyaluronic acid preparation, resiniferatoxin preparation, botulinum toxin preparation, etc. with expectations such as mucosa repair, anti-inflammatory activity, anti-allergic activity and suppression of activation of C-fiber are carried out. In the case of internal agent, improvement in symptom by a cholinolytic agent which is an agent for pollakiuria which suppresses the movement of bladder smooth muscle is exceptional. Although administration of pentosan polysulfate sodium (Elmiron [registered trade mark]) which is a heparin analog with expectations of repairing and anti-inflammatory activities, and administration of antidepressant, analgesic/anti-inflammatory agent, antispasmodic agent, anti-histaminic agent and anti-allergic agent with expectations such as analgesic activity, anti-inflammatory activity and anti-allergic activity have been carried out, no useful treating agent has been found yet.

Prostaglandin (PG) $E_2$ has been known as a metabolite in the arachidonate cascade. It has been known that $PGE_2$ possesses cyto-protective activity, uterine contractive activity, a pain-inducing effect, a promoting effect on digestive peristalsis, an awakening effect, a suppressive effect on gastric acid secretion, hypotensive activity and diuretic activity and so on.

A recent study has proved existence of various $PGE_2$ subtype receptors possessing a different physiological or pharmacological role from each other. At present, four receptor subtypes are known and they are called $EP_1$, $EP_2$, $EP_3$, and $EP_4$ (Negishi M., et al., *J. Lipid Mediators Cell Signaling;* 12, 379-391 (1995)).

With regard to the finding for PG and urination symptom, topical intravesical therapy by $PGE_1$ or $PGE_2$ was tried for hemorrhagic cystitis by administration of cyclophosphamide which is an anti-cancer agent. Although prevention of getting serious of cystitis, hemostatic effect and the like were demonstrated, it is known the fact that symptom of bladder irritation was induced at the same time (*Rinsho Ketsueki*, volume 36, no. 8, page 728, published in 1995), that intravesical injection of $PGE_2$ and $EP_1$ and $EP_3$ agonists to healthy persons induce symptom of bladder irritation (*Urological Research*, volume 18, no. 5, page 349, published in 1990) and that an intravesical injection therapy of $PGE_2$ with an object of promotion of urination to patients suffering from urinary retention is effective (*European Urology*, volume 4, no. 5, page 366, published in 1978). They show that compounds which acts on $PGE_2$ receptors have promotion of urination function (worsening of urine accumulation symptom) and recovery from cystitis (reduction of urine accumulation symptom), which are contrary each other.

Among $PGE_2$ receptors, it is known that compounds which have antagonistic activity to $EP_1$ are useful as preventive and/or treatment agents for pollakiuria (refer to WO 03/43655) and are useful as preventive and/or treatment agents for urinary incontinence (refer to WO 02/15902).

However, it isn't reported that $EP_4$ agonist relates to lower urinary tract diseases.

DISCLOSURE OF THE INVENTION

Cystitis among lower urinary tract diseases has the symptoms of pollakiuria, urgency of urination, pain and/or discomfort in the reproductive organs and/or lower urinary tract. Especially, for the pain in the reproductive organs and/or lower urinary tract, only the symptomatic therapy to relieve pain is known up to the present time. That is, a useful treatment is not found in the current state though the development of the effective treatment for the lower urinary tract diseases is hoped.

From the view, the development of an agent which is safe and has no side effect for preventing and/or treating the lower urinary tract diseases by new mechanism is desired.

The present inventors have energetically studied to find that (1) $EP_4$ agonist improves the symptom of pollakiuria without increasing function of urination in the model of cyclophosphamide-induced inflammation in lower urinary tract in rats, (2) because the intravesical injection of $EP_1$ agonist and $EP_3$ agonist induces stimulation of bladder, selective $EP_4$ agonist is useful as a preventive and/or treatment agent for the lower urinary tract diseases without side effect, (3) $EP_4$ agonist improves bladder capacity and/or bladder compliance, (4) $EP_4$ agonist protects bladder mucosa and/or bladder epithelial cells and/or promotes the regeneration thereof, and have completed the present invention.

That is, the present invention relates to:

1 an agent for preventing and/or treating lower urinary tract disease, comprising $EP_4$ agonist, 2 the agent according to the above 1, wherein the lower urinary tract disease is inflammation in lower urinary tract, 3 the agent according to the above 2, wherein the lower urinary tract disease is cystitis and/or urethritis, 4 the agent according to the above 3, wherein the cystitis is interstitial cystitis, 5 the agent according to the above 1, wherein one or more symptoms selected from (1) pollakiuria, (2) urgency of urination, (3) hematuria and (4) pain and/or discomfort in the reproductive organs and/or lower urinary tract is/are improved, 6 the agent according to the above 5, wherein the pain in the reproductive organs and/or lower urinary tract is bladder pain, urinary tract pain, vulvar pain, vaginal pain, scrotal pain, perineal pain or pelvic pain, 7 the agent according to the above 1, wherein the lower urinary tract disease is a disease induced by one or more selected from the group consisting of stimulation to bladder, inflammation of bladder and fibrosis of bladder, 8 an agent for improving bladder compliance and/or bladder capacity comprising $EP_4$ agonist 9 an agent for protecting bladder mucosa and/or bladder epithelial cells and/or promoting the regeneration thereof, comprising $EP_4$ agonist, 10 the agent according to any one of the above 1, 8 and 9, which comprises the $EP_4$ agonist and one kind or more kinds agent(s) selected from heparin preparation, dimethylsulfoxide preparation, hyaluronic acid preparation, resiniferatoxin preparation, botulinum toxin preparation, pentosan polysulfate sodium, antidepressant, antibiotics, analgesic/anti-inflammatory agent, antispasmodic agent, anti-histaminic agent, anti-allergic agent, $EP_1$ antagonist and $EP_3$ antagonist in combination, 11 the agent according to any one of the above 1, 8 and 9, wherein the $EP_4$ agonist is a compound represented by formula (I):

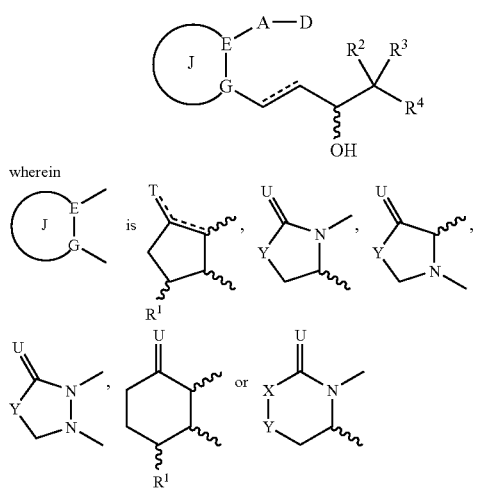

wherein T is an oxygen atom, a halogen atom or an acyloxy group which may have a substituent(s), $R^1$ is a hydrogen atom, a hydroxy group, a C1-6 alkyloxy group or a C1-6 acyloxy group, U is an oxygen atom or a sulfur atom, X and Y are each independently a methylene group, an oxygen atom, a sulfur atom, or a nitrogen atom which may have a substituent(s) wherein X and Y are not simultaneously an oxygen atom, a sulfur atom nor a nitrogen atom which may have a substituent(s), A is a spacer of which main chain has an atom number of 1-8 and which may have a substituent(s), D is an acidic group which may be protected, $R^2$ and $R^3$ are each independently an alkyl group which may have a substituent(s) or a halogen atom, $R^4$ is a cyclic ring group which may have a substituent(s) or an aliphatic hydrocarbon group which may have a substituent(s), ⋰ is a single bond or a double bond, wherein continuous double bonds are not formed, ⌇ is α-configuration or β-configuration or a mixture thereof having an optional mixing ratio, a salt thereof, an N-oxide thereof or a solvate thereof, or a prodrug thereof, or a cyclodextrin clathrate thereof, 12 the agent according to any one of the above 1, 8 and 9, wherein the $EP_4$ agonist is a compound represented by formula (IA)

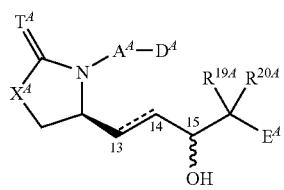

wherein ⋰ is (1) a single bond or (2) a double bond,
$R^{19A}$ and $R^{20A}$ are each independently, (1) a hydrogen atom, (2) C1-10 alkyl or (3) a halogen atom,
$T^A$ is (1) an oxygen atom or (2) a sulfur atom,
$X^A$ is (1) —$CH_2$—, (2) —O— or (3) —S—,
$A^A$ is $A^{1A}$ or $A^{2A}$, $A^{1A}$ is (1) C2-8 straight-chain alkylene which may be substituted by 1 to 2 C1-4 alkyl, (2) C2-8 straight-chain alkenylene which may be substituted by 1 to 2 C1-4 alkyl or (3) C2-8 straight-chain alkynylene which may be substituted by 1 to 2 C1-4 alkyl, $A^{2A}$ is -$G^{1A}$-$G^{2A}$-$G^{3A}$-, $G^{1A}$ is (1) C1-4 straight-chain alkylene which may be substituted by 1 to 2 C1-4 alkyl, (2) C2-4 straight-chain alkenylene which may be substituted by 1 to 2 C1-4 alkyl or (3) C2-4 straight-chain alkynylene which may be substituted by 1 to 2 C1-4 alkyl, $G^{2A}$ is (1) —$Y^A$—, (2) -(ring$1^A$)-, (3) —$Y^A$-(ring$1^A$)-, (4) -(ring$1^A$)-$Y^A$— or (5) —$Y^A$—(C1-4 alkylene)-(ring$1^A$)-, $Y^A$ is (1) —S—, (2) —SO—, (3) —$SO_2$—, (4) —O— or (5) —$NR^{1A}$—, $R^{1A}$ is (1) a hydrogen atom, (2) C1-10 alkyl or (3) C2-10 acyl, $G^{3A}$ is (1) a bond, (2) C1-4 straight-chain alkylene which may be substituted by 1 to 2 C1-4 alkyl, (3) C2-4 straight-chain alkenylene which may be substituted by 1 to 2 C1-4 alkyl or (4) C2-4 straight-chain alkynylene which may be substituted by 1 to 2 C1-4 alkyl, $D^A$ is $D^{1A}$ or $D^{2A}$, $D^{1A}$ is (1) —COOH, (2) —$COOR^{2A}$, (3) tetrazol-5-yl or (4) $CONR^{3A}SO_2R^{4A}$, $R^{2A}$ is (1) C1-10 alkyl, (2) phenyl, (3) C1-10 alkyl substituted by phenyl or (4) biphenyl, $R^{3A}$ is (1) a hydrogen atom or (2) C1-10 alkyl, $R^{4A}$ is (1) C1-10 alkyl or (2) phenyl, $D^{2A}$ is (1) —$CH_2OH$, (2) —$CH_2OR^{5A}$, (3) hydroxy, (4) —$OR^{5A}$, (5) formyl, (6) —$CONR^{6A}R^{7A}$, (7) —$CONR^{6A}SO_2R^{8A}$, (8) —CO—(NH-amino acid residue-CO)$_{mA}$—OH, (9) —O—(CO-amino acid residue-NH)$_{mA}$—H, (10) —$COOR^{9A}$, (11) —OCO—$R^{10A}$, (12) —COO—$Z^{1A}$—$Z^{2A}$—$Z^{3A}$, (13)

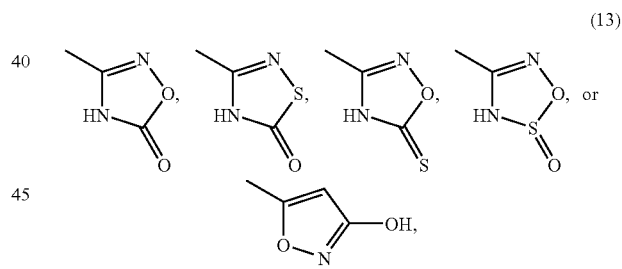

$R^{5A}$ is C1-10 alkyl, $R^{6A}$ and $R^{7A}$ are each independently, (1) a hydrogen atom or (2) C1-10 alkyl, $R^{8A}$ is C1-10 alkyl substituted by phenyl, $R^{9A}$ is (1) C1-10 alkyl substituted by biphenyl which may be substituted by 1 to 3 C1-10 alkyl, C1-10 alkoxy or a halogen atom or (2) biphenyl substituted by 1 to 3 C1-10 alkyl, C1-10 alkoxy or a halogen atom, $R^{10A}$ is (1) phenyl or (2) C1-10 alkyl, mA is 1 or 2, $Z^{1A}$ is (1) C1-15 alkylene, (2) C2-15 alkenylene or (3) C2-15 alkynylene, $Z^{2A}$ is (1) —CO—, (2) —OCO—, (3) —COO—, (4) —$CONR^{11A}$—, (5) —$NR^{12A}CO$—, (6) —O—, (7) —S—, (8) —SO—, (9) —$SO_2$—, (10) —$NR^{13A}$—, (11) —$NR^{14A}CONR^{15A}$—, (12) —$NR^{16A}COO$—, (13) —$OCONR^{17A}$— or (14) —OCOO—, $Z^{3A}$ is (1) a hydrogen atom, (2) C1-15 alkyl, (3) C2-15 alkenyl, (4) C2-15 alkynyl, (5) ring$2^A$ or (6) C1-10 alkyl substituted by C1-10 alkoxy, C1-10 alkylthio, C1-10 alkyl-NR$^{18A}$— or ring$2^A$, $R^{11A}$, $R^{12A}$, $R^{13A}$, $R^{14A}$, $R^{15A}$, $R^{16A}$, $R^{17A}$ and $R^{18A}$ are each independently (1) a hydrogen atom or (2) C1-15 alkyl, $R^{11A}$ and $Z^{3A}$ may be taken together with the nitrogen atom to which they are attached to form a 5- to 7-membered saturated mono-heterocyclic ring, and the heterocyclic ring may contain other one hetero atom selected from oxygen, nitrogen and sulfur atom, $E^A$ is $E^{1A}$ or $E^{2A}$, $E^{1A}$ is (1) C3-7 cycloalkyl or (2) ring$3^A$, $E^{2A}$ is (1) C3-7 cycloalkyl, (2) ring$4^A$ or (3) ring$5^A$, ring$1^A$ and ring$5^A$ may be substituted by 1 to 3 $R^{21A}$ and/or $R^{22A}$, ring$3^A$ may be optionally substituted by 1 to 2 $R^{21A}$, C3-7 cycloalkyl represented by $E^{2A}$ is substituted by one of $R^{21A}$ or $R^{22A}$, which may be substituted by another 1 to 2 $R^{21A}$ and/or $R^{22A}$, ring$4^A$ is substituted by one of $R^{22A}$, which may be substituted by another 1 to 2 $R^{21A}$ and/or $R^{22A}$, which may be substituted by heterocyclic ring formed by $R^{11A}$, $Z^{3A}$ and the nitrogen to which $Z^{3A}$ is attached or ring$2^A$ may be substituted by $R^{23A}$, $R^{21A}$ is (1) C1-10 alkyl, (2) C1-10 alkoxy, (3) halogen atom, (4) nitro, (5) C1-10 alkyl substituted by 1 to 3 halogen atom(s) or (6) phenyl, $R^{22A}$ is (1) C2-10 alkenyl, (2) C2-10 alkynyl, (3) C1-10 alkylthio, (4) hydroxy, (5) —NR$^{24A}$R$^{25A}$, (6) C1-10 alkyl substituted by C1-10 alkoxy, (7) C1-10 alkyl substituted by C1-10 alkoxy substituted by 1 to 3 halogen atom(s), (8) C1-10 alkyl substituted by —NR$^{24A}$R$^{25A}$, (9) ring$6^A$, (10) —O-ring$7^A$, (11) C1-10 alkyl substituted by ring$7^A$, (12) C2-10 alkenyl substituted by ring$7^A$, (13) C2-10 alkynyl substituted by ring$7^A$, (14) C1-10 alkoxy substituted by ring$7^A$, (15) C1-10 alkyl substituted by —O-ring$7^A$, (16) —COOR$^{26A}$ or (17) C1-10 alkoxy substituted by 1 to 3 halogen atom(s), $R^{24A}$, $R^{25A}$ and $R^{26A}$ are each independently, (1) a hydrogen atom or (2) C1-10 alkyl, $R^{23A}$ is (1) C1-15 alkyl, (2) C2-15 alkenyl, (3) C2-15 alkynyl or (4) C1-10 alkyl substituted by C1-10 alkoxy, C1-10 alkylthio or C1-10 alkyl-NR$^{27A}$—, $R^{27A}$ is (1) a hydrogen atom or (2) C1-10 alkyl, ring$1^A$, ring$2^A$, ring$5^A$, ring$6^A$ and ring$7^A$ are (1) C3-15 mono-, bi- or tri-carbocyclic aryl which may be partially or fully saturated or (2) 3 to 15 membered mono-, bi- or tri-heterocyclic aryl containing 1 to 4 hetero atom selected from oxygen, nitrogen and sulfur atom(s) which may be partially or fully saturated, ring$3^A$ and ring$4^A$ are (1) thienyl, (2) phenyl or (3) furyl, ring$6^A$ and ring$7^A$ may be substituted by 1 to 3 $R^{28A}$, $R^{28A}$ is (1) C1-10 alkyl, (2) C2-10 alkenyl, (3) C2-10 alkynyl, (4) C1-10 alkoxy, (5) C1-10 alkyl substituted by C1-10 alkoxy, (6) a halogen atom, (7) hydroxy, (8) C1-10 alkyl substituted by 1 to 3 halogen atom(s) or (9) C1-10 alkyl substituted by C1-10 alkoxy substituted by 1 to 3 halogen atom(s), and wherein (1) when $T^A$ is an oxygen atom, $X^A$ is CH$_2$—, $A^A$ is $A^{1A}$, and $D^A$ is $D^{1A}$, $E^A$ is $E^{2A}$, (2) ring$5^A$ is not C3-7 cycloalkyl, phenyl, thienyl nor furyl, (3) when ring$6^A$ is phenyl, the phenyl is substituted by at least one $R^{28A}$, a salt thereof, an N-oxide thereof or a solvate thereof, or a prodrug thereof, or a cyclodextrin clathrate thereof, 13 the agent according to any one of the above 1, 8 and 9, wherein the EP$_4$ agonist is a compound represented by formula (IB):

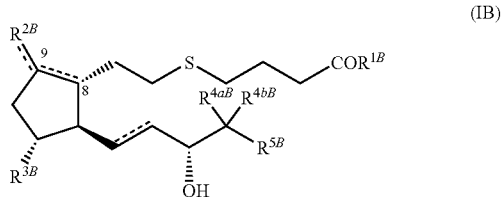

(IB)

wherein R$^{1B}$ is hydroxy, C1-6 alkyloxy or NR$^{6B}$R$^{7B}$ in which R$^{6B}$ and R$^{7B}$ are each independently hydrogen or C1-4 alkyl, R$^{2B}$ is oxygen atom, halogen atom or O—COR$^{8B}$ in which R$^{8B}$ is C1-4 alkyl, phenyl or phenyl(C1-4 alkyl), R$^{3B}$ is hydrogen atom or hydroxy, R$^{4aB}$ and R$^{4bB}$ are each independently a hydrogen atom or C1-4 alkyl, R$^{5B}$ is phenyl substituted with the following substituent(s):

i) 1 to 3 selected from (a) C1-4 alkyloxy-C1-4 alkyl, (b) C2-4 alkenyloxy-C1-4 alkyl, (c) C2-4 alkynyloxy-C1-4 alkyl, (d) C3-7 cycloalkyloxy-C1-4 alkyl, (e) C3-7 cycloalkyl (C1-4 alkyloxy)-C1-4 alkyl, (f) phenyloxy-C1-4 alkyl, (g) phenyl-C1-4 alkyloxy-C1-4 alkyl, (h) C1-4 alkylthio-C1-4 alkyl, (i) C2-4 alkenylthio-C1-4 alkyl, (j) C2-4 alkynylthio-C1-4 alkyl, (k) C3-7 cycloalkylthio-C1-4 alkyl, (l) C3-7 cycloalkyl(C1-4 alkylthio)-C1-4 alkyl, (m) phenylthio-C1-4 alkyl and (n) phenyl-C1-4 alkylthio-C1-4 alkyl, ii) (a) C1-4 alkyloxy-C1-4 alkyl and C1-4 alkyl, (b) C1-4 alkyloxy-C1-4 alkyl and C1-4 alkyloxy, (c) C1-4 alkyloxy-C1-4 alkyl and hydroxy, (d) C1-4 alkyloxy-C1-4 alkyl and a halogen atom, (e) C1-4 alkylthio-C1-4 alkyl and C1-4 alkyl, (f) C1-4 alkylthio-C1-4 alkyl and C1-4 alkyloxy, (g) C1-4 alkylthio-C1-4 alkyl and hydroxy or (h) C1-4 alkylthio-C1-4 alkyl and a halogen atom, iii) (a) haloalkyl or (b) hydroxy-C1-4 alkyl, or iv) C1-4 alkyl and hydroxy;

is a single bond or double bond, wherein continuous double bonds are not formed and wherein when R$^{2B}$ is O—COR$^{8B}$, the 8-9 position represents a double bond, a salt thereof, an N-oxide thereof or a solvate thereof, or a prodrug thereof, or a cyclodextrin clathrate thereof, 14 the agent according to any one of 1, 8 and 9, wherein the EP$_4$ agonist is the compound selected from ({3-[((1R,2S,3R)-3-hydroxy-2-{(1E,3S)-3-hydroxy-4-[3-(methoxymethyl)phenyl]but-1-enyl}-5-oxocyclopentyl) sulfanyl]propyl}sulfanyl)acetic acid;

4-{[2-((1R,2R,3R)-3-hydroxy-2-{(1E,3S)-3-hydroxy-4-[3-(methoxymethyl)phenyl]but-1-enyl}-5-oxocyclopentyl) ethyl]sulfanyl}butanoic acid;

7-((1R,2R,3R)-3-hydroxy-2-{(1E,3S)-3-hydroxy-4-[3-(methoxymethyl)phenyl]but-1-enyl}-5-oxocyclopentyl) heptanoic acid;

(5Z)-7-((1R,2R,3R)-2-{(1E,3S)-4-[3-(ethoxymethyl)phenyl]-3-hydroxybut-1-enyl}-3-hydroxy-5-oxocyclopentyl) hept-5-enoic acid;

(5Z)-7-((1R,2R,3R,5R)-5-chloro-2-{(1E,3S)-4-[3-(ethoxymethyl)phenyl]-3-hydroxybut-1-enyl}-3-hydroxycyclopentyl)hept-5-enoic acid;

4-[(2-{(1R,2R,3R)-3-hydroxy-2-[(1E,3S)-3-hydroxy-4-(4-hydroxy-3-methylphenyl)but-1-enyl]-5-oxocyclopentyl}ethyl)sulfanyl]butanoic acid;

methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate;

4-{[2-((1R,2R)-2-{(1E,3S)-3-hydroxy-4-[3-(methoxymethyl)phenyl]but-1-enyl}-5-oxocyclopentyl)ethyl]sulfanyl}butanoic acid;

4-[(2-{(2R)-2-[(1E,3S)-4-(3-chlorophenyl)-3-hydroxybut-1-enyl]-5-oxopyrrolidin-1-yl}ethyl)sulfanyl]butanoic acid;

4-{[2-((2R)-2-{(1E,3S)-3-hydroxy-4-[3-(trifluoromethyl)phenyl]but-1-enyl}-5-oxopyrrolidin-1-yl)ethyl]sulfanyl}butanoic acid;

4-[(2-{(2R)-2-[(1E,3S)-4-(4-fluorophenyl)-3-hydroxybut-1-enyl]-5-oxopyrrolidin-1-yl}ethyl)sulfanyl]butanoic acid;

4-[(2-{(2R)-2-[(1E,3S)-3-hydroxy-4-(2-naphthyl)but-1-enyl]-5-oxopyrrolidin-1-yl}ethyl)sulfanyl]butanoic acid;

4-[(2-{(4S)-4-[(1E,3S)-4-(4-fluorophenyl)-3-hydroxy-1-butenyl]-2-oxo-1,3-oxazolidin-3-yl}ethyl)sulfanyl]butanoic acid;

2-[(2-{(2R)-2-[(1E,3S)-3-hydroxy-4-(3-methylphenyl)but-1-enyl]-5-oxopyrrolidin-1-yl}ethyl)sulfanyl]-1,3-thiazole-4-carboxylic acid;

2-(2-{(2R)-2-[(1E,3S)-3-hydroxyoct-1-enyl]-5-oxopyrrolidin-1-yl}ethyl)sulfanyl]-1,3-thiazole-4-carboxylic acid;

2-{[2-((2R)-2-{(1E,3S)-4-[3-(1-benzofuran-2-yl)phenyl]-3-hydroxybut-1-enyl}-5-oxopyrrolidin-1-yl)ethyl]sulfanyl}-1,3-thiazole-4-carboxylic acid;

4-[(2-{(2R)-2-[(1E,3S)-3-hydroxyoct-1-enyl]-5-oxopyrrolidin-1-yl}ethyl)sulfanyl]butanoic acid;

{[3-({(1R,2S,3R)-3-hydroxy-2-[(1E,3S)-3-hydroxyoct-1-enyl]-5-oxocyclopentyl}sulfanyl)propyl]sulfanyl}acetic acid; and 2-[(2-{(4S)-4-[(1E,3S)-4-(4-fluorophenyl)-3-hydroxybut-1-enyl]-2-oxo-1,3-oxazolidin-3-yl}ethyl)sulfanyl]-1,3-thiazole-4-carboxylic acid, a salt thereof, an N-oxide thereof or a solvate thereof, or a prodrug thereof, or a cyclodextrin clathrate thereof, 15 a method for preventing and/or treating lower urinary tract disease, which comprises administering an effective amount of $EP_4$ agonist to a mammal, 16 a method for improving bladder compliance and/or bladder capacity which comprises administering effective amount of $EP_4$ agonist to a mammal, 17 a method for protecting and/or promoting the regeneration of bladder mucosa and/or bladder epithelial cells, which comprises administering an effective amount of $EP_4$ agonist to a mammal, 18 Use of $EP_4$ agonist for preparing an agent for preventing and/or treating lower urinary tract disease, 19 Use of $EP_4$ agonist for preparing an agent for improving bladder compliance and/or bladder capacity, and 20 Use of $EP_4$ agonist for preparing an agent for protecting and/or promoting the regeneration of bladder mucosa and/or bladder epithelial cells.

In the specification, the "cyclic ring" in the "cyclic ring group which may have a substituent(s)" represented by $R^4$ includes, for example, carbocyclic ring or heterocyclic ring. The carbocyclic ring includes, for example, C3-15 mono- or poly-carbocyclic ring, spiro-linked poly-carbocyclic ring or bridged poly-carbocyclic ring etc. C3-15 mono- or poly-carbocyclic ring includes C3-15 mono- or poly-carbocyclic ring which is unsaturated or saturated partially or fully thereof. For example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene ring etc. are included. Spiro-linked poly-carbocyclic ring includes, for example, spiro[4.4]nonane, spiro[4.5]decane, spiro[5.5]undecane ring etc. Bridged polycarbocyclic ring includes, for example, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, noradamantane ring etc. Among them, C3-15 mono- or polyaromatic carbocyclic ring includes, for example, benzene, azulene, naphthalene, phenanthrene, anthracene ring etc. Heterocyclic ring includes, for example, 3 to 15 membered mono- or poly-heterocyclic ring, spiro-linked poly-heterocyclic ring or bridged poly-heterocyclic ring. These rings comprise 1 to 5 hetero atom(s) selected from oxygen, nitrogen and/or sulfur. 3 to 15 membered mono- or poly-heterocyclic ring which comprises 1 to 5 hetero atom(s) selected from oxygen, nitrogen and/or sulfur includes 3 to 15 membered mono- or poly-heterocyclic ring comprising 1 to 5 hetero atom(s) selected from oxygen, nitrogen and/or sulfur, which is unsaturated or saturated partially or fully thereof. For example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazohne, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane ring etc. are included. Spiro-linked bi-heterocyclic ring includes, for example, azaspiro[4.4]nonane, azaspiro[4.5]decane, azaspiro[5.5]undecane ring etc. Bridged biheterocyclic ring includes, for example, azabicyclo[2.2.1]heptane, azabicyclo[3.1.1]heptane, azabicyclo[3.2.1]octane, azabicyclo[2.2.2]octane ring etc. Among them, 3 to 15 membered mono-, bi- or tri-aromatic heterocyclic ring which comprises 1 to 5 hetero atom(s) selected from oxygen, nitrogen and/or sulfur includes for example pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine ring etc.

The "substituent" in the "cyclic ring group which may have a substituent(s)" represented by $R^4$ includes, for example, (a) alkyl group which may have a substituent(s), (b) alkenyl group which a may have substituent(s), (c) alkynyl group which may have a substituent(s), (d) carbocyclic ring which may have a substituent(s), (e) heterocyclic ring may have a substituent(s), (f) hydroxy group may have a substituent(s), (g) thiol group which may have a substituent(s), (h) amino group which may have a substituent(s), (i) carbamoyl group which may have a substituent(s), (j) sulfamoyl group which may have a substituent(s), (k) carboxy group, (l) alkoxycarbonyl group (for example, C1-6 alkoxycarbonyl such as methoxycarbonyl, ethoxycarbonyl, t-butoxycarbonyl etc.), (m) sulfo group (—SO$_3$H), (n) sulfino group (—SO$_2$H), (o) phosphono group (—PO(OH)$_2$), (p) nitro group, (q) oxo group, (r) thioxo group, (s) cyano group, (t) amidino group, (u) imino group, (v) —B(OH)$_2$ group, (w) halogen group, (for example, fluorine, chlorine, bromine, iodine etc.), (x) alkylsulfinyl group (for example, C1-6 alkylsulfinyl group such as methylsulfinyl, ethylsulfinyl etc.), (y) arylsulfinyl group (for example, C6-10 arylsulfinyl group such as phenylsulfinyl etc.), (z) alkylsulfonyl group (for example, C1-6 alkylsulfonyl group such as methylsulfonyl, ethylsulfonyl etc.), (aa) arylsulfonyl (for example, C6-10 arylsulfonyl such as phenylsulfonyl etc.), (bb) acyl group (for example, C1-10 alkanoyl such as formyl, acetyl, propanoyl, pivaroyl etc., C6-10 arylcarbonyl such as benzoyl etc.) etc. These optional substituents may be substituted 1-5 at the replaceable position.

The "alkyl group" in "alkyl group which may have a substituent(s)" as the substituent includes, for example, straight or branched C1-15 alkyl group such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl group etc.

The substituent of alkyl group includes hydroxy group, amino group, carboxy group, cyano group, nitro group, mono- or di-C1-10 alkylamino group (for example, methylamino, ethylamino, propylamino, dimethylamino, diethylamino etc.), C1-10 alkoxy group (for example, methoxy, ethoxy, propoxy, isopropoxy, t-butoxy, hexyloxy, octyloxy, decanyloxy etc), C1-6 acyloxy group (for example, acetyloxy, ethanoyloxy, propanoyloxy, butanoyloxy, pentanoyloxy, hexanoyloxy group etc.), C1-10 alkylcarbonyloxy group (for example, acetoxy, ethylcarbonyloxy etc.), carbocyclic ring (it has the same meaning as the above-mentioned carbocyclic ring in the "cyclic ring" of the "cyclic ring group which may have a substituent(s)".), heterocyclic ring (it has the same meaning as the above-mentioned heterocyclic ring in the "cyclic ring" of the "cyclic ring group which may have a substituent(s)".), halogen atom (it has the same meaning as mentioned above.), C1-10 alkoxy substituted by 1 to 3 halogen atom(s) (for example, monofluoromethoxy group, difluoromethoxy group, trifluoromethoxy group etc.), —O-carbocyclic ring (it has the same meaning as the above-mentioned carbocyclic ring in the "cyclic ring" of the "cyclic ring group which may have a substituent(s)".), and —O-heterocyclic ring (it has the same meaning as the above-mentioned heterocyclic ring in the "cyclic ring" of the "cyclic ring group which may have a substituent(s)".) etc. These optional substituents may be substituted 1-4 at the replaceable position.

The "alkenyl group" in "alkenyl group which may have a substituent(s)" as the substituent includes, for example, straight or branched C2-15 alkenyl group such as ethenyl, propenyl, butenyl, butadienyl, pentenyl, pentadienyl, hexenyl, hexadienyl, heptenyl, heptadienyl, octenyl, octadienyl, nonenyl, nonadienyl, decenyl, decadienyl, undecenyl, dodecenyl, tridecenyl, tetradecenyl, pentadecenyl etc. The substituent of alkenyl group has the same meaning as the above-mentioned the substituent in "alkyl group which may have a substituent(s)".

The "alkynyl group" in "alkynyl group which may have a substituent(s)" as the substituent includes, for example, straight or branched C2-15 alkynyl group such as ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl, decadiynyl, undecynyl, dodecynyl, tridecynyl, tetradecynyl, pentadecynyl etc. The substituent of alkynyl group has the same meaning as the above-mentioned the substituent in "alkyl group which may have a substituent(s)".

The "carbocyclic ring" in "carbocyclic ring which may have a substituent(s)" as the substituent has the same meaning as the above-mentioned carbocyclic ring in the "cyclic ring" of the "cyclic ring group which may have a substituent(s)". The substituent of carbocyclic ring includes, for example, straight or branched C1-15 alkyl group (it has the same meaning as the above-mentioned alkyl group of the "alkyl group which may have a substituent(s)".), straight or branched C2-15 alkenyl group (it has the same meaning as the above-mentioned alkenyl group of the "alkenyl group which may have a substituent(s)".), straight or branched C2-15 alkynyl group (it has the same meaning as the above-mentioned alkynyl group of the "alkynyl group which may have a substituent(s)".), hydroxy group, C1-6 alkoxy group (for example, methoxy, ethoxy, propoxy, isopropoxy, butoxy, isobutyloxy, tert-butoxy, pentyloxy, hexyloxy etc.), thiol group, C1-6 alkylthio group (for example, methylthio, ethylthio, propylthio, isopropylthio, butylthio, isobutylthio, isobutylthio, tert-butylthio, pentylthio, hexylthio etc.), amino group, mono- or di-C1-6 alkylamino group (for example, methylamino, ethylamino, propylamino, isopropylamino, butylamino, isobutylamino, tert-butylamino, pentylamino, hexylamino, dimethylamino, diethylamino, dipropylamino, N-methyl-N-ethylamino etc), halogen atom (it has the same meaning as mentioned above.), cyano group, nitro group, trifluoromethyl group, trifluoromethoxy group etc. These optional substituents may be substituted 1-5 at the replaceable position.

The "heterocyclic ring" in "heterocyclic ring which may have a substituent(s)" as the substituent has the same meaning as the above-mentioned heterocyclic ring in the "cyclic ring" of the "cyclic ring group which may have a substituent(s)".

The "substituent" in "hydroxy group which may have a substituent(s)", "thiol group which may have a substituent(s)" and "amino group which may have a substituent(s)" as the substituent includes, for example, (i) alkyl group which may have a substituent(s) (it has the same meaning as mentioned above.), (ii) alkenyl group which may have a substituent(s) (it has the same meaning as mentioned above.), (iii) alkynyl group which may have a substituent(s) (it has the same meaning as mentioned above.), (iv) carbocyclic ring which may have a substituent(s) (it has the same meaning as mentioned above.), (v) heterocyclic ring which may have a substituent(s) (it has the same meaning as mentioned above.), (vi) acyl group (for example, C1-6 alkanoyl group such as formyl, acetyl, propanoyl, pivaloyl, butanoyl, pentanoyl, hexanoyl etc. or isomer thereof, or C6-10 aromatic carbocyclic ring carbonyl such as benzoyl etc.), (vii) carbamoyl group which may have a substituent(s) (it has the same meaning as mentioned below.), (viii) alkylsulfonyl group (for example, C1-6 alkyl sulfonyl group such as methylsulfonyl, ethylsulfonyl etc.), (ix) arylsulfonyl group (for example, C6-10 arylsulfonyl such as phenylsulfonyl etc.).

The "carbamoyl group which may have a substituent(s)" as the substituent includes carbamoyl group which have no substituent, N-mono-C1-6 alkylcarbamoyl (for example, N-methylcarbamyl, N-ethylcarbamyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl etc.), N-mono-C6-10 arylcarbamyl such as N-phenylcarbamoyl etc., N,N-di-C1-6 alkylcarbamoyl (for example, N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl etc.), N-di-C6-10 arylcarbamoyl such as N,N-diphenylcarbamoyl etc., N—C6-10 aryl-N—C1-6 alkylcarbamoyl (for example, N-phenyl-N-methylcarbamoyl, N-phenyl-N-ethylcarbamoyl, N-phenyl-N-propylcarbamoyl, N-phenyl-N-butylcarbamoyl, N-phenyl-N-pentylcarbamoyl, N-phenyl-N-hexylcarbamoyl etc.).

The "sulfamoyl group which may have a substituent(s)" as the substituent includes sulfamoyl group which have no substituent, N-mono-C1-6 alkylsulfamoyl (for example, N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl etc.), N-mono-C6-10 arylsulfamoyl such as N-phenylsulfamoyl etc., N,N-di-C1-6 alkylsulfamoyl (for example, N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl etc.), N-di-C6-10 arylsulfamoyl such as N,N-diphenylsulfamoyl etc., N—C6-10 aryl-N—C1-6 alkylsulfamoyl (for example, N-phenyl-N-methylsulfamoyl, N-phenyl-N-ethylsulfamoyl, N-phenyl-N-propylsulfamoyl, N-phenyl-N-butylsulfamoyl, N-phenyl-N-pentylsulfamoyl, N-phenyl-N-hexylsulfamoyl etc.).

In the specification, the "aliphatic hydrocarbon group which may have a substituent(s)" represented by $R^4$ includes, for example, alkyl group which may have a substituent(s), alkenyl group which may have a substituent(s) or alkynyl group which may have a substituent(s). The "alkyl group which may have a substituent(s)", the "alkenyl group which may have a substituent(s)" or the "alkynyl group which may have a substituent(s)" has the same meaning as the above-mentioned "alkyl group which may have a substituent(s)", "alkenyl group which may have a substituent(s)" or "alkynyl group which may have a substituent(s)" defined in substituent of cyclic ring.

In the specification, the "C1-6 alkyloxy group" represented by $R^1$ includes, for example, methoxy, ethoxy, propoxy, butoxy, pentyloxy, hexyloxy etc.

In the specification, the "C1-6 acyloxy group" represented by $R^1$ includes, for example, acetyloxy, ethanoyloxy, propanoyloxy, butanoyloxy, pentanoyloxy, hexanoyloxy etc.

In the specification, the "alkyl group which may have a substituent(s)" represented by $R^2$ or $R^3$ has the same meaning as the above-mentioned "alkyl group which may have a substituent(s)" defined in $R^4$.

In the specification, the "halogen atom" represented by $R^2$ or $R^3$ has the same meaning as mentioned above.

In the specification, the "halogen atom" represented by T has the same meaning as mentioned above.

In the specification, the "acyloxy group" in "acyloxy group which may have a substituent(s)" represented by T includes, for example, C1-10 alkanoyloxy group such as acetyloxy, propanoyloxy, pivaloyloxy etc. The "substituent" in "acyloxy group which may have a substituent(s)" represented by T has the same meaning as the above-mentioned "alkyl group which may have a substituent(s)" defined in $R^4$.

In the specification, the "substituent" in "nitrogen atom which may have a substituent(s)" represented by X and Y includes "alkyl group which may have a substituent(s)" or "cyclic ring group which may have a substituent(s)". The "alkyl group which may have a substituent(s)" or the "cyclic ring which may have a substituent(s)" has the same meaning as the above-mentioned "alkyl group which may have a substituent(s)" or "cyclic ring group which may have a substituent(s)" defined in $R^4$.

In the specification, the "spacer of which main chain has an atom number of 1-8" in "spacer of which main chain has an atom number of 1-8 and which may have a substituent(s)" represented by A means the distance that 1-8 atom(s) of main chain is(are) connected. In this case, the "atom number of main chain" should be counted atom number of main chain to become minimal. For example, the atom number is counted as 4 or 3 in 1,4-phenylene or 1,3-phenylene respectively.

The "spacer of which main chain has an atom number of 1-8" includes, for example, C1-8 alkylene, C2-8 alkenylene, C2-8 alkynylene, cyclic ring etc. The carbon atom in these groups may be replaced with 1 to 5 oxygen atom, nitrogen atom, sulfur atom, carbonyl group, thiocarbonyl group, sulfinyl group or sulfonyl group at replaceable positions structurally. C1-8 alkylene group includes, for example, methylene, ethylene, trimethylene, tetramethylene, pentamethylene, hexamethylene, heptamethylene, octamethylene etc. C2-8 alkenylene includes, for example, ethenylene, propenylene, butenylene, butadienylene, pentenylene, pentadienylene, hexenylene, hexadienylene, heptenylene, heptadienylene, octenylene, octadienylene etc. C2-8 alkynylene group includes, for example, ethynylene, propynylene, butynylene, butadiynylene, pentynylene, pentadiynylene, hexynylene, hexadiynylene, heptynylene, heptadiynylene, octynylene, octadiynylene etc. The cyclic ring has the same meaning as the above-mentioned "cyclic ring" in "cyclic ring group which may have a substituent(s)" defined in $R^4$. The "substituent" in "spacer of which main chain has an atom number of 1-8 and which may have a substituent(s)" has the same meaning as the above-mentioned "substituent" in "alkyl group which may have a substituent(s)". These optional substituents may be substituted 1-10, preferably 1-5, more preferably 1-3 at the replaceable position.

In the specification, the "acidic group which may be protected" represented by D represents the "acidic group" which may be protected by a "protecting group". Examples of the "acidic group" include (a) hydroxy group, (b) formyl group (—CHO), (c) alkoxy group (for example, C1-6 alkoxy group such as methoxy, ethoxy, propoxy, isopropoxy, butoxy, isobutyloxy, tert-butoxy, pentyloxy, hexyloxy etc., C6-10 aryloxy such as phenoxy), (d) carboxy (—COOH), (e) sulfo (—$SO_3H$), (f) sulfonamide (—$SO_2NH_2$ or —$NR^{101}SO_3H$ ($R^{101}$ is hydrogen atom or alkyl group which may have a substituent(s). (it has the same meaning as the above-mentioned "alkyl group which may have a substituent(s)" defined in $R^4$.)), (g) phosphono (—$PO(OH)_2$), (h) phenol (—$C_6H_4OH$), (i) —$CONR^{101}SO_3H$ ($R^{101}$ has the same meaning as mentioned above.), (j) amido (—$CONH_2$) or (k) various types of Brønsted acid such as a nitrogen-containing ring residue having hydrogen from which can be removed as proton. The "Brønsted acid" means a substance which gives hydrogen ion to other substance. Examples of the "nitrogen-containing ring residue having hydrogen from which can be removed as proton" include:

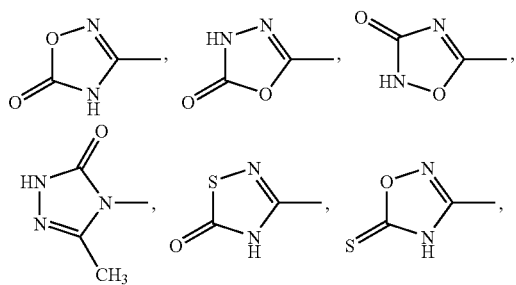

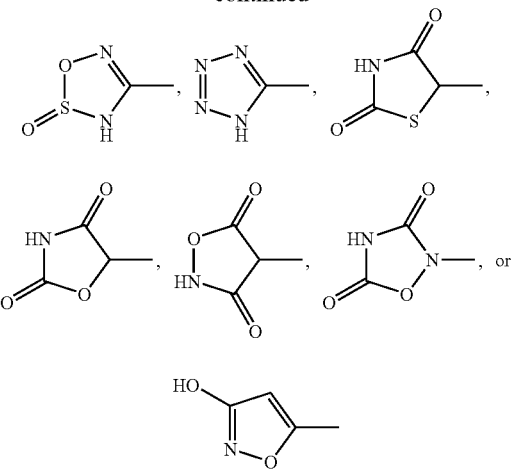

etc. Preferred as "acidic group" is carboxy group or hydroxy group. More preferred is carboxy group. The "protecting group" in "acidic group which may be protected" represented by D includes (a) alkyl group which may have a substituent(s) (it has the same meaning as the above-mentioned "alkyl group which may have a substituent(s)" defined in $R^4$), (b) cyclic ring group which may have a substituent(s) (it has the same meaning as the above-mentioned "cyclic ring group which may have a substituent(s)" defined in $R^4$), (c) amino group which may have a substituent(s) (it has the same meaning as the above-mentioned "amino group which may have a substituent(s)" defined in $R^4$), (d) amino acid, (e) acyl group which may have a substituent(s) etc. The "acyl group" in "acyl group which may have a substituent(s)" has the same meaning as the above-mentioned "acyl group" defined in $R^4$. The "substituent" in "acyl group which may have a substituent(s)" has the same meaning as the above-mentioned substituent in "alkyl group which may have a substituent(s)" defined in $R^4$. The "amino acid" means a natural amino acid or unnatural amino acid residue. The natural amino acid or unnatural amino acid residue includes, for example, glycine, alanine, valine, leucine, isoleucine, serine, threonine, cystein, methionine, proline, asparagine, glutamine, phenylalanine, tyrosine, tryptophan, aspartic acid, glutamic acid, lysine, arginine, histidine, β-alanine, cystathionine, cystine, homoserine, isoleucine, lanthionine, norleucine, norvaline, ornithine, sarcosine, thyronine etc. When the amino acid contains an amino group, the amino acid which is substituted by the above-mentioned substituent of amino group is included.

$EP_4$ agonists in the present invention do not only include ones which have ever been found but ones which will be found from now. $EP_4$ agonists which have ever been found include, for example, the compounds described in the following (A)-(W).

(A) In the pamphlet of WO03/009872, it is described that the compound represented by the following formula (IA) has $EP_4$ agonistic activity. As well, the definition of each group of the compound represented by formula (IA) is described in the pamphlet of WO03/009872 in detail. Accordingly, $EP_4$ agonist of the present invention includes the compound represented by formula (IA):

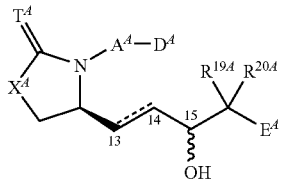
(IA)

wherein ⌇ is (1) a single bond or (2) a double bond,
$R^{19A}$ and $R^{20A}$ are each independently, (1) a hydrogen atom, (2) C1-10 alkyl or (3) a halogen atom,
$T^A$ is (1) an oxygen atom or (2) a sulfur atom,
$X^A$ is (1) —$CH_2$—, (2) —O— or (3) —S—,
$A^A$ is $A^{1A}$ or $A^{2A}$,
$A^{1A}$ is (1) C2-8 straight-chain alkylene which may be substituted by 1 to 2 C1-4 alkyl, (2) C2-8 straight-chain alkenylene which may be substituted by 1 to 2 C1-4 alkyl or (3) C2-8 straight-chain alkynylene which may be substituted by 1 to 2 C1-4 alkyl,
$A^{2A}$ is -$G^{1A}$-$G^{2A}$-$G^{3A}$-,
$G^{1A}$ is (1) C1-4 straight-chain alkylene which may be substituted by 1 to 2 C1-4 alkyl, (2) C2-4 straight-chain alkenylene which may be substituted by 1 to 2 C1-4 alkyl or (3) C2-4 straight-chain alkynylene which may be substituted by 1 to 2 C1-4 alkyl,
$G^{2A}$ is (1) —$Y^A$—, (2) -(ring$1^A$)-, (3) —$Y^A$—(ring$1^A$)-, (4) -(ring$1^A$)-$Y^A$— or (5) —$Y^A$—(C1-4 alkylene)-(ring$1^A$)-,
$Y^A$ is (1) —S—, (2) —SO—, (3) —$SO_2$—, (4) —O— or (5) —$NR^{1A}$—,
$R^{1A}$ is (1) a hydrogen atom, (2) C1-10 alkyl or (3) C2-10 acyl,
$G^{3A}$ is (1) a bond, (2) C1-4 straight-chain alkylene which may be substituted by 1 to 2 C1-4 alkyl, (3) C2-4 straight-chain alkenylene which may be substituted by 1 to 2 C1-4 alkyl or (4) C2-4 straight-chain alkynylene which may be substituted by 1 to 2 C1-4 alkyl,
$D^A$ is $D^{1A}$ or $D^{2A}$,
$D^{1A}$ is (1) —COOH, (2) —COOR$^{2A}$, (3) tetrazol-5-yl or (4) CONR$^{3A}SO_2R^{4A}$,
$R^{2A}$ is (1) C1-10 alkyl, (2) phenyl, (3) C1-10 alkyl substituted by phenyl or (4) biphenyl,
$R^{3A}$ is (1) a hydrogen atom or (2) C1-10 alkyl,
$R^{4A}$ is (1) C1-10 alkyl or (2) phenyl,
$D^{2A}$ is (1) —$CH_2OH$, (2) —$CH_2OR^{5A}$, (3) hydroxy, (4) —OR$^{5A}$, (5) formyl, (6) —CONR$^{6A}R^{7A}$, (7) —CONR$^{6A}SO_2R^{8A}$, (8) —CO—(NH-amino acid residue-CO)$_{mA}$—OH, (9) —O—(CO-amino acid residue-NH)$_{mA}$—H, (10) —COOR$^{9A}$, (11) —OCO—R$^{10A}$, (12) —COO—$Z^{1A}$-$Z^{2A}$-$Z^{3A}$, (13)

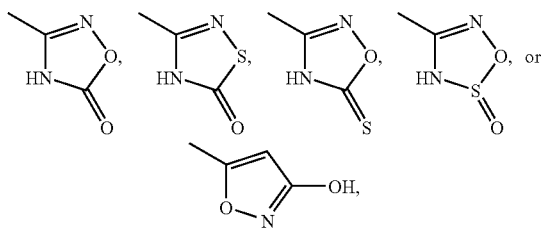
(13)

$R^{5A}$ is C1-10 alkyl,
$R^{6A}$ and $R^{7A}$ are each independently, (1) a hydrogen atom or (2) C1-10 alkyl,
$R^{8A}$ is C1-10 alkyl substituted by phenyl,
$R^{9A}$ is (1) C1-10 alkyl substituted by biphenyl which may be substituted by 1 to 3 C1-10 alkyl, C1-10 alkoxy or a halogen atom or (2) biphenyl substituted by 1 to 3 C1-10 alkyl, C1-10 alkoxy or halogen atom,
$R^{10A}$ is (1) phenyl or (2) C1-10 alkyl,
mA is 1 or 2,
$Z^{1A}$ is (1) C1-15 alkylene, (2) C2-15 alkenylene or (3) C2-15 alkynylene,
$Z^{2A}$ is (1) —CO—, (2) —OCO—, (3) —COO—, (4) —CONR$^{11A}$—, (5) —NR$^{12A}$CO—, (6) —O—, (7) —S—, (8) —SO—, (9) —$SO_2$—, (10) —NR$^{13A}$—, (11) —NR$^{14A}$CONR$^{15A}$—, (12) —NR$^{16A}$COO—, (13) —OCONR$^{17A}$— or (14) —OCOO—,
$Z^{3A}$ is (1) a hydrogen atom, (2) C1-15 alkyl, (3) C2-15 alkenyl, (4) C2-15 alkynyl, (5) ring$2^A$ or (6) C1-10 alkyl substituted by C1-10 alkoxy, C1-10 alkylthio, C1-10 alkyl-NR$^{18A}$— or ring$2^A$,
$R^{11A}$, $R^{12A}$, $R^{13A}$, $R^{14A}$, $R^{15A}$, $R^{16A}$, $R^{17A}$ and $R^{18A}$ are each independently (1) a hydrogen atom or (2) C1-15 alkyl,
$R^{11A}$ and $Z^{3A}$ may be taken together with the nitrogen atom to which they are attached to form a 5- to 7-membered saturated mono-heterocyclic ring, and the heterocyclic ring may contain other one hetero atom selected from oxygen, nitrogen and sulfur atoms,
$E^A$ is $E^{1A}$ or $E^{2A}$,
$E^{1A}$ is (1) C3-7 cycloalkyl or (2) ring$3^A$,
$E^{2A}$ is (1) C3-7 cycloalkyl, (2) ring$4^A$ or (3) ring$5^A$,
ring$1^A$ and ring$5^A$ may be substituted by 1 to 3 $R^{21A}$ and/or $R^{22A}$,
ring$3^A$ may be substituted by 1 to 2 $R^{21A}$,
C3-7 cycloalkyl represented by $E^{2A}$ is substituted by one of $R^{21A}$ or $R^{22A}$, which may be substituted by another 1 to 2 $R^{21A}$ and/or $R^{22A}$,
ring$4^A$ is substituted by one of $R^{22A}$, which may be substituted by another 1 to 2 $R^{21A}$ and/or $R^{22A}$, which may be substituted by heterocyclic ring formed by $R^{11A}$,
$Z^{3A}$ and the nitrogen to which $Z^{3A}$ is attached or ring$2^A$ may be substituted by $R^{23A}$,
$R^{21A}$ is (1) C1-10 alkyl, (2) C1-10 alkoxy, (3) halogen atom, (4) nitro, (5) C1-10 alkyl substituted by 1 to 3 halogen atom(s) or (6) phenyl,
$R^{22A}$ is (1) C2-10 alkenyl, (2) C2-10 alkynyl, (3) C1-10 alkylthio, (4) hydroxy, (5) —NR$^{24A}R^{25A}$, (6) C1-10 alkyl substituted by C1-10 alkoxy, (7) C1-10 alkyl substituted by C1-10 alkoxy substituted by 1 to 3 halogen atom(s), (8) C1-10 alkyl substituted by —NR$^{24A}R^{25A}$, (9) ring$6^A$, (10) —O-ring$7^A$, (11) C1-10 alkyl substituted by ring$7^A$, (12) C2-10 alkenyl substituted by ring$7^A$, (13) C2-10 alkynyl substituted by ring$7^A$, (14) C1-10 alkoxy substituted by ring$7^A$, (15) C1-10 alkyl substituted by —O-ring$7^A$, (16) —COOR$^{26A}$ or (17) C1-10 alkoxy substituted by 1 to 3 halogen atom(s),
$R^{24A}$, $R^{25A}$ and $R^{26A}$ are each independently, (1) a hydrogen atom or (2) C1-10 alkyl,
$R^{23A}$ is (1) C1-15 alkyl, (2) C2-15 alkenyl, (3) C2-15 alkynyl or (4) C1-10 alkyl substituted by C1-10 alkoxy, C1-10 alkylthio or C1-10 alkyl-NR$^{27A}$—,
$R^{27A}$ is (1) a hydrogen atom or (2) C1-10 alkyl,
ring$1^A$, ring$2^A$, ring$5^A$, ring$6^A$ and ring$7^A$ are (1) C3-15 mono-, bi- or tri-carbocyclic aryl which may be partially or fully saturated or (2) 3- to 15-membered mono-, bi- or tri-heterocyclic aryl containing 1 to 4 hetero atom(s) selected from oxygen, nitrogen and sulfur atom(s) which may be partially or fully saturated, ring$3^A$ and ring$4^A$ are (1) thienyl, (2) phenyl or (3) furyl,
ring$6^A$ and ring$7^A$ may be substituted by 1 to 3 $R^{28A}$,
$R^{28A}$ is (1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxy, (8) C1-10 alkyl substituted by 1 to 3 halogen atom(s) or (9) C1-10 alkyl substituted by C1-10 alkoxy substituted by 1 to 3 halogen atom(s), and wherein (1) when $T^A$ is an oxygen atom, $X^A$ is $CH_2$—, $A^A$ is $A^{1A}$, and $D^A$ is $D^{1A}$, $E^A$ is $E^{2A}$, (2) ring$5^A$ is not C3-7 cycloalkyl, phenyl, thienyl nor furyl, (3) when ring$6^A$ is phenyl, the phenyl is substituted by at least one $R^{28A}$, a salt thereof, an N-oxide thereof or a solvate thereof, or a prodrug thereof, or a cyclodextrin clathrate thereof.

(B) In the pamphlet of WO00/003980, it is described that the compound represented by the following formula (IB) has $EP_4$ agonistic activity. As well, the definition of each group of the compound represented by formula (IB) is described in the pamphlet of WO00/003980 in detail. Accordingly, $EP_4$ agonist of the present invention includes the compound represented by formula (IB):

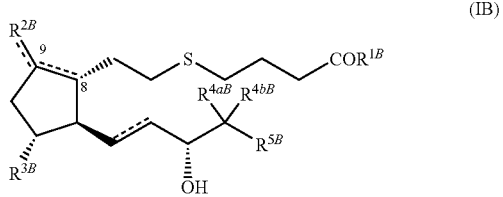

(IB)

wherein $R^{1B}$ is hydroxy, C1-6 alkyloxy or $NR^{6B}R^{7B}$ in which $R^{6B}$ and $R^{7B}$ are each independently hydrogen or C1-4 alkyl, $R^{2B}$ is oxygen atom, halogen atom or O—$COR^{8B}$ in which $R^{8B}$ is C1-4 alkyl, phenyl or phenyl(C1-4 alkyl), $R^{3B}$ is hydrogen atom or hydroxy, $R^{4aB}$ and $R^{4bB}$ are each independently hydrogen atom or C1-4 alkyl, $R^{5B}$ is phenyl substituted with the following substituent(s):

i) 1 to 3 selected from (a) C1-4 alkyloxy-C1-4 alkyl, (b) C2-4 alkenyloxy-C1-4 alkyl, (c) C2-4 alkynyloxy-C1-4 alkyl, (d) C3-7 cycloalkyloxy-C1-4 alkyl, (e) C3-7 cycloalkyl (C1-4 alkyloxy)-C1-4 alkyl, (f) phenyloxy-C1-4 alkyl, (g) phenyl-C1-4 alkyloxy-C1-4 alkyl, (h) C1-4 alkylthio-C1-4 alkyl, (i) C2-4 alkenylthio-C1-4 alkyl, (j) C2-4 alkynylthio-C1-4 alkyl, (k) C3-7 cycloalkylthio-C1-4 alkyl, (l) C3-7 cycloalkyl(C1-4 alkylthio)-C1-4 alkyl, (m) phenylthio-C1-4 alkyl and (n) phenyl-C1-4 alkylthio-C1-4 alkyl, ii) (a) C1-4 alkyloxy-C1-4 alkyl and C1-4 alkyl, (b) C1-4 alkyloxy-C1-4 alkyl and C1-4 alkyloxy, (c) C1-4 alkyloxy-C1-4 alkyl and hydroxy, (d) C1-4 alkyloxy-C1-4 alkyl and halogen atom, (e) C1-4 alkylthio-C1-4 alkyl and C1-4 alkyl, (f) C1-4 alkylthio-C1-4 alkyl and C1-4 alkyloxy, (g) C1-4 alkylthio-C1-4 alkyl and hydroxy or (h) C1-4 alkylthio-C1-4 alkyl and a halogen atom, iii) (a) haloalkyl or (b) hydroxy-C1-4 alkyl, or iv) C1-4 alkyl and hydroxy;

⇌ is a single bond or double bond, wherein continuous double bonds are not formed and wherein when $R^{2B}$ is O—$COR^{8B}$, the 8-9 position represents a double bond, a salt thereof, an N-oxide thereof or a solvate thereof, or a prodrug thereof, or a cyclodextrin clathrate thereof.

(C) In the specification of EP855389, it is described that the compound represented by the following formula (IC) has $EP_4$ agonistic activity. As well, the definition of each group of the compound represented by formula (IC) is described in the specification of EP855389 in detail. Accordingly, $EP_4$ agonist of the present invention includes the compound represented by formula (IC):

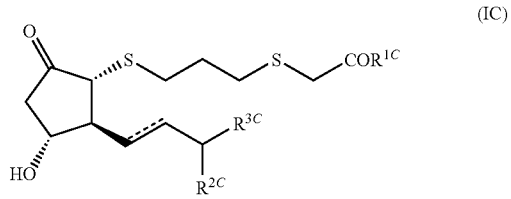

(IC)

wherein $R^{1C}$ is hydroxy, C1-4 alkoxy or $NR^{6C}R^{7C}$ wherein $R^{6C}$ and $R^{7C}$ are each independently hydrogen atom or C1-4 alkyl, $R^{2C}$ is a hydrogen atom or hydroxy, $R^{3C}$ is (i) C1-8 alkyl, C2-8 alkenyl, or C2-8 alkynyl, (ii) phenyl or C3-7 cycloalkyl, (iii) C1-8 alkyl, C2-8 alkenyl, or C2-8 alkynyl substituted by phenyl or C3-7 cycloalkyl wherein when $R^{2C}$ is hydrogen atom, alkyl, alkenyl or alkynyl in (i) and (iii) may be substituted by one hydroxy, ⇌ is double bond or single bond wherein the formula including the 8-epi equilibrium compound thereof, a salt thereof, an N-oxide thereof or a solvate thereof, or a prodrug thereof, or a cyclodextrin clathrate thereof.

(D) In the specification of EP985663, it is described that the compound represented by the following formula (ID) has $EP_4$ agonistic activity. As well, the definition of each group of the compound represented by formula (ID) is described in the specification of EP985663 in detail. Accordingly, $EP_4$ agonist of the present invention includes the compound represented by formula (ID):

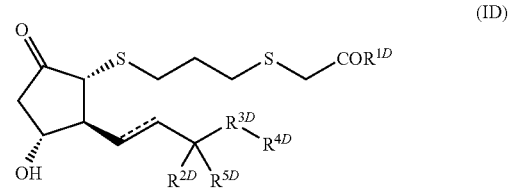

(ID)

wherein $R^{1D}$ is hydroxy, C1-6 alkyloxy or $NR^{6D}R^{7D}$ wherein $R^{6D}$ and $R^{7D}$ are each independently a hydrogen atom or C1-6 alkyl;

$R^{2D}$ is a hydrogen atom or hydroxy;

$R^{3D}$ is a bond or C1-6 alkylene;

$R^{4D}$ is (i) C1-8 alkyl, C2-8 alkenyl or C2-8 alkynyl substituted by 1 to 3 substituents selected from C1-6 alkyloxy and halogen atom(s), (ii) phenyloxy or C3-7 cycloalkyloxy, (iii) furyl, furyloxy, thienyl, thienyloxy, naphthyl, naphthyloxy, phthalanyl or phthalanyloxy, (iv) phenyl, phenyloxy, C3-7 cycloalkyl or C3-7 cycloalkyloxy substituted by 1 to 3 substituent(s) selected from the following groups of (1) to (40): (1) C1-6 alkyl, (2) C2-6 alkenyl, (3) C2-6 alkynyl, (4) C1-6 alkyloxy, (5) C1-6 alkyloxy-C1-6 alkyl, (6) C1-6 alkyloxy-C1-6 alkyloxy, (7) C2-6 alkenyloxy-C1-6 alkyl, (8) C1-6 alkyl substituted by 1 to 3 hydroxy, (9) C1-6 alkyl substituted by 1 to 3 halogen atom(s), (10) C1-6 alkylthio, (11) C1-6 alkylthio-C1-6 alkyl, (12) C1-6 alkylthio-C1-6 alkyloxy, (13) C2-6 alkenylthio-C1-6 alkyl, (14) C1-6 alkylsulfonyl, (15) halogen atom, (16) trihalomethyl, (17) cyano, (18) nitro, (19) amino, (20) hydroxy, (21) C3-7 cycloalkyl, (22) C3-7 cycloalkyloxy, (23) C3-7 cycloalkyl-C1-6 alkyl, (24) C3-7 cycloalkyloxy-C1-6 alkyl, (25) phenyl, (26) phenyloxy, (27) phenyl-C1-6 alkyl, (28) phenyl-C2-6 alkenyl, (29) phenyl-C2-6 alkynyl, (30) phenyloxy-C1-6 alkyl, (31) phenyloxy-C2-6 alkenyl, (32) phenyloxy-C2-6 alkynyl, (33) furyl, (34) furyloxy, (35) furyl-C1-6 alkyl, (36) furyloxy-C1-6 alkyl, (37) thienyl, (38) thienyloxy, (39) thienyl-C1-6 alkyl or (40) thienyloxy-C1-6 alkyl (the above mentioned phenyl, furyl, thienyl and cycloalkyl are optionally substituted by 1 to 3 substituents selected from C1-6 alkyl, C1-6 alkyloxy, C1-6 alkyloxy-C1-6 alkyl, nitro, halogen, trihalomethyl, amino and hydroxy); or (v) furyl, furyloxy, thienyl, thienyloxy, naphthyl, naphthyloxy, phthalanyl or phthalanyloxy substituted by 1 to 3 substituent(s) selected from the following groups: (1) C1-6 alkyl, (2) C2-6 alkenyl, (3) C2-6 alkynyl, (4) C1-6 alkyloxy, (5) C1-6 alkyloxy-C1-6 alkyl, (6) C1-6 alkyloxy-C1-6 alkyloxy, (7) C2-6 alkenyloxy-C1-6 alkyl, (8) C1-6 alkyl substituted by 1 to 3 hydroxy, (9) C1-6 alkyl substituted by 1 to 3 halogen atom(s), (10) C1-6 alkylthio, (11) C1-6 alkylthio-C1-6 alkyl, (12) C1-6 alkylthio-C1-6 alkyloxy, (13) C2-6 alkenylthio-C1-6 alkyl, (14) C1-6 alkylsulfonyl, (15) halogen atom, (16) trihalomethyl, (17) cyano, (18) nitro, (19) amino, (20) hydroxy, (21) C3-7 cycloalkyl, (22) C3-7 cycloalkyloxy, (23) C3-7 cycloalkyl-C1-6 alkyl, (24) C3-7 cycloalkyloxy-C1-6 alkyl, (25) phenyl, (26) phenyloxy, (27) phenyl-C1-6 alkyl, (28) phenyl-C2-6 alkenyl, (29) phenyl-C2-6 alkynyl, (30) phenyloxy-C1-6 alkyl, (31) phenyloxy-C2-6 alkenyl, (32) phenyloxy-C2-6 alkynyl, (33) furyl, (34) furyloxy, (35) furyl-C1-6 alkyl, (36) furyloxy-C1-6 alkyl, (37) thienyl, (38) thienyloxy, (39) thienyl-C1-6 alkyl or (40) thienyloxy-C1-6 alkyl whewinthe above mentioned phenyl, furyl, thienyl and cycloalkyl may be substituted by 1 to 3 substituent(s) selected from C1-6 alkyl, C1-6 alkyloxy, C1-6 alkyloxy-C1-6 alkyl, nitro, halogen, trihalomethyl, amino and hydroxy;

$R^{5D}$ is hydrogen atom or C1-6 alkyl;

⋰ is double bond or single bond wherein $R^{2D}$ is hydrogen atom, C1-6 alkylene represented by $R^{3D}$ may be substituted by one hydroxy, a salt thereof, an N-oxide thereof or a solvate thereof, or a prodrug thereof, or a cyclodextrin clathrate thereof.

(E) In the pamphlet of WO00/015608, it is described that the compound represented by the following formula (IE) has $EP_4$ agonistic activity. As well, the definition of each group of the compound represented by formula (IE) is described in the pamphlet of WO00/015608 in detail. Accordingly, $EP_4$ agonist of the present invention includes the compound represented by formula (IE):

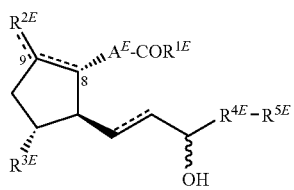

(IE)

wherein $A^E$ is C2-8 alkylene, C2-8 alkenylene, C1-4 alkylene-phenylene or C2-4 alkenylene-phenylene, $R^{1E}$ is hydroxy, C1-6 alkyloxy, C1-6 alkyloxy-C1-6 alkyloxy, HO—C1-6 alkyloxy, or a formula of $NR^{6E}R^{7E}$ wherein $R^{6E}$ and $R^{7E}$ are each independently hydrogen atom or C1-4 alkyl.

$R^{2E}$ is an oxygen atom, a halogen atom or $R^{8E}$—COO— wherein $R^{8E}$ is a hydrogen atom, C1-4 alkyl, phenyl or phenyl (C1-4 alkyl), C1-4 alkyloxy, HOOC—C1-4 alkyl, C1-4 alkyloxy-carbonyl-C1-4 alkyl, HOOC—C2-4 alkenyl, or C1-4 alkyloxy-carbonyl-C2-4 alkenyl, $R^{3E}$ is a hydrogen atom or hydroxy, $R^{4E}$ is C1-4 alkylene, $R^{5E}$ is phenyl substituted by the following groups of i) to iv):

i) 1 to 3 selected from (1) C1-4 alkyloxy-C1-4 alkyl, (2) C2-4 alkenyloxy-C1-4 alkyl, (3) C2-4 alkynyloxy-C1-4 alkyl, (4) C3-7 cycloalkyloxy-C1-4 alkyl, (5) C3-7 cycloalkyl (C1-4 alkyloxy)-C1-4 alkyl, (6) phenyloxy-C1-4 alkyl, (7) phenyl-C1-4 alkyloxy-C1-4 alkyl, (8) C1-4 alkylthio-C1-4 alkyl, (9) C2-4 alkenylthio-C1-4 alkyl, (10) C2-4 alkynylthio-C1-4 alkyl, (11) C3-7 cycloalkylthio-C1-4 alkyl, (12) C3-7 cycloalkyl(C1-4 alkylthio)-C1-4 alkyl, (13) phenylthio-C1-4 alkyl or (14) phenyl-C1-4 alkylthio-C1-4 alkyl, ii) (1) C1-4 alkyloxy-C1-4 alkyl and C1-4 alkyl, (2) C1-4 alkyloxy-C1-4 alkyl and C1-4 alkyloxy, (3) C1-4 alkyloxy-C1-4 alkyl and hydroxy, (4) C1-4 alkyloxy-C1-4 alkyl and a halogen atom, (5) C1-4 alkylthio-C1-4 alkyl and C1-4 alkyl, (6) C1-4 alkylthio-C1-4 alkyl and C1-4 alkyloxy, (7) C1-4 alkylthio-C1-4 alkyl and hydroxy or (8) C1-4 alkylthio-C1-4 alkyl and halogen atom, iii) (1) halo-C1-4 alkyl or (2) hydroxy-C1-4 alkyl or iv) C1-4 alkyl and hydroxy;

⋰ is a single bond or double bond, and wherein double bonds are not formed wherein when $R^{2E}$ is $R^{8E}$—COO—, $R^{1E}$ is C1-6 alkyloxy, C1-6 alkyloxy-C1-6 alkyloxy or HO—C1-6 alkyloxy and the bond in the 8-9 position is a double bond, a salt thereof, an N-oxide thereof or a solvate thereof, or a prodrug thereof, or a cyclodextrin clathrate thereof.

(F) In the pamphlet of WO01/149661, it is described that the compound represented by the following formula (IF) has $EP_4$ agonistic activity. As well, the definition of each group of the compound represented by formula (IF) is described in the pamphlet of WO01/149661 in detail. Accordingly, $EP_4$ agonist of the present invention includes the compound represented by formula (IF):

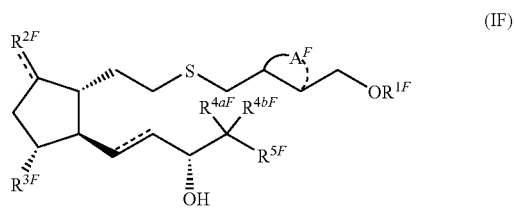

(IF)

wherein $-A^F-$ is absent or $-A^F-$ is methylene or ethylene, $R^{1F}$ is a hydrogen atom, C1-6 alkyl, phenyl-C1-6 alkyl, C2-6 alkanoyl or phenyl-C2-6 alkanoyl, $R^{2F}$ is an oxygen atom or a halogen atom, $R^{3F}$ is a hydrogen atom or hydroxy, $R^{4aF}$ and $R^{4bF}$ are each independently a hydrogen atom or C1-4 alkyl, $R^{5F}$ is phenyl substituted with the following group of i) to iv):

i) 1 to 3 selected from (1) C1-4 alkyloxy-C1-4 alkyl, (2) C2-4 alkenyloxy-C1-4 alkyl, (3) C2-4 alkynyloxy-C1-4 alkyl, (4) C3-7 cycloalkyloxy-C1-4 alkyl, (5) C3-7 cycloalkyl (C1-4 alkyloxy)-C1-4 alkyl, (6) phenyloxy-C1-4 alkyl, (7) phenyl-C1-4 alkyloxy-C1-4 alkyl, (8) C1-4 alkylthio-C1-4 alkyl, (9) C2-4 alkenylthio-C1-4 alkyl, (10) C2-4 alkynylthio-C1-4 alkyl, (11) C3-7cycloalkylthio-C1-4 alkyl, (12) C3-7 cycloalkyl(C1-4 alkylthio)-C1-4 alkyl, (13) phenylthio-C1-4 alkyl or (14) phenyl-C1-4 alkylthio-C1-4 alkyl, ii) (1) C1-4 alkyloxy-C1-4 alkyl and C1-4 alkyl, (2) C1-4 alkyloxy-C1-4 alkyl and C1-4alkyloxy, (3) C1-4 alkyloxy-C1-4 alkyl and hydroxy, (4) C1-4 alkyloxy-C1-4 alkyl and a halogen atom, (5) C1-4 alkylthio-C1-4 alkyl and C1-4 alkyl, (6) C1-4 alkylthio-C1-4 alkyl and C1-4 alkyloxy, (7) C1-4 alkylthio-C1-4 alkyl and hydroxy or (8) C1-4 alkylthio-C1-4 alkyl and a halogen atom, iii) haloalkyl or hydroxy-C1-4 alkyl, or iv) C1-4 alkyl and hydroxy;

≡ is a single bond or double bond, a salt thereof, an N-oxide thereof or a solvate thereof, or a prodrug thereof, or a cyclodextrin clathrate thereof.

(G) In the pamphlet of WO01/166518, it is described that the compound represented by the following formula (IG) has EP$_4$ agonistic activity. As well, the definition of each group of the compound represented by formula (IG) is described in the pamphlet of WO01/166518 in detail. Accordingly, EP$_4$ agonist of the present invention includes the compound represented by formula (IG):

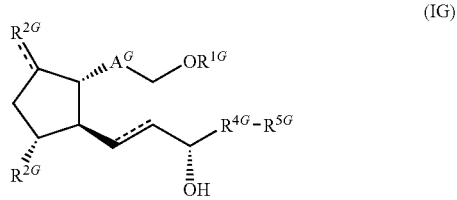

(IG)

wherein $A^G$ is C2-8 alkylene, C2-8 alkenylene, C1-4 alkylene-phenylene or C2-4 alkenylene-phenylene, $R^{1G}$ is a hydrogen atom, C1-6 alkyl, phenyl-C1-6 alkyl, C2-6 alkanoyl, phenyl-C2-6 alkanoyl, $R^{2G}$ is an oxygen atom or a halogen atom, $R^{3G}$ is a hydrogen atom or hydroxy, $R^{4G}$ is C1-4 alkylene, $R^{5G}$ is phenyl substituted with the following group of i) to iv):

i) 1 to 3 selected from (1) C1-4 alkyloxy-C1-4 alkyl, (2) C2-4 alkenyloxy-C1-4 alkyl, (3) C2-4 alkynyloxy-C1-4 alkyl, (4) C3-7 cycloalkyloxy-C1-4 alkyl, (5) C3-7 cycloalkyl (C1-4 alkyloxy)-C1-4 alkyl, (6) phenyloxy-C1-4 alkyl, (7) phenyl-C1-4 alkyloxy-C1-4 alkyl, (8) C1-4 alkylthio-C1-4 alkyl, (9) C2-4 alkenylthio-C1-4 alkyl, (10) C2-4 alkynylthio-C1-4 alkyl, (11) C3-7 cycloalkylthio-C1-4 alkyl, (12) C3-7 cycloalkyl(C1-4 alkylthio)-C1-4 alkyl, (13) phenylthio-C1-4 alkyl or (14) phenyl-C1-4 alkylthio-C1-4 alkyl, ii) (1) C1-4 alkyloxy-C1-4 alkyl and C1-4 alkyl, (2) C1-4 alkyloxy-C1-4 alkyl and C1-4 alkyloxy, (3) C1-4 alkyloxy-C1-4 alkyl and hydroxy, (4) C1-4 alkyloxy-C1-4 alkyl and halogen atom, (5) C1-4 alkylthio-C1-4 alkyl and C1-4 alkyl, (6) C1-4 alkylthio-C1-4 alkyl and C1-4 alkyloxy, (7) C1-4 alkylthio-C1-4 alkyl and hydroxy or (8) C1-4 alkylthio-C1-4 alkyl and a halogen atom, iii) (1) halo C1-4 alkyl or (2) hydroxyl C1-4 alkyl, or iv) C1-4 alkyl and hydroxy;

≡ is a single bond or double bond, a salt thereof, an N-oxide thereof or a solvate thereof, or a prodrug thereof, or a cyclodextrin clathrate thereof.

(H) In the pamphlet of WO2004/065365, it is described that the compound represented by the following formula (IH) has EP$_4$ agonistic activity. As well, the definition of each group of the compound represented by formula (IH) is described in the pamphlet of WO2004/065365 in detail. Accordingly, EP$_4$ agonist of the present invention includes the compound represented by formula (IH):

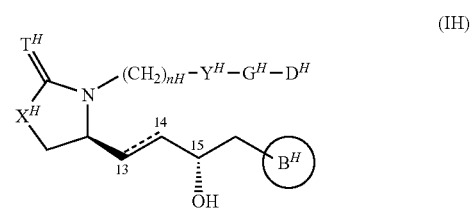

(IH)

wherein ⌇ is a single bond or double bond,

⌇ is α-configuration, β-configuration or a voluntary ratio mixture thereof, $D^H$ is —COOR$^{1H}$ or tetrazolyl, $R^{1H}$ is a hydrogen atom or C1-4 alkyl, $G^H$ is ringA$^H$ or C1-4 alkylene, ringA$^H$ is

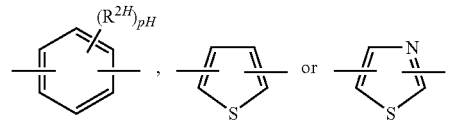

wherein $R^{2H}$ is halogen atom, C1-4 alkyl or C1-4 alkoxy, pH is 0 or an integer of 1 to 4 and when pH is more than 2, each of $R^{2H}$ is same or different, $Y^H$ is a bond or —S—, $T^H$ is oxygen atom or sulfur atom, $X^H$ is —CH$_2$—, —O— or —S—, ringB$^H$ is C3-7 cycloalkyl which may have a substituent(s),

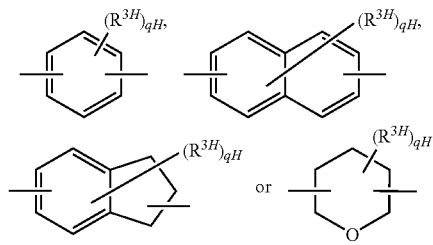

wherein $R^{3H}$ is (1) a halogen atom, (2) C1-4 alkyl which may be substituted by 1 to 5 halogen atom(s), (3) C1-4 alkoxyl which may be substituted by 1 to 5 halogen atom(s), (4) C1-4 alkyl substituted by C1-4 alkoxy, (5) phenyl or (6) 3 to 15 membered mono-, bi- or tri-heterocyclic ring which comprises 1-4 hetero atom(s) selected from oxygen, nitrogen and sulfur, and may be saturated partially or fully, (5) phenyl or (6) heterocyclic ring in $R^{3H}$ may be substituted by 1 to 3 substituent(s) selected form (a) halogen atom, (b) C1-4 alkyl, (c) C1-4 alkoxy and/or (d) nitro, qH is 0 or an integer of 1 to 5, when qH is more than 2, each $R^{3H}$ may be same or different
nH is an integer of 1 to 4,
a salt thereof, an N-oxide thereof or a solvate thereof, or a prodrug thereof, or a cyclodextrin clathrate thereof.

(J) In the pamphlet of WO02/24647, it is described that the compound represented by the following formula (IJ) has $EP_4$ agonistic activity. As well, the definition of each group of the compound represented by formula (IJ) is described in the pamphlet of WO02/24647 in detail. Accordingly, $EP_4$ agonist of the present invention includes the compound represented by formula (IJ):

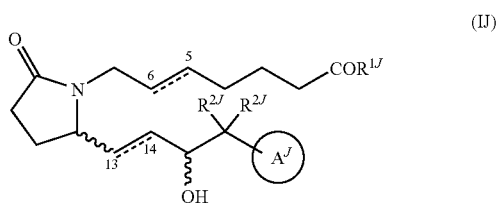

wherein $R^{1J}$ is hydroxy, C1-4 alkoxy, $NHSO_2$—C1-4 alkyl, or NHCO-phenyl, $A^J$ is benzene or thiophene, two $R^{2J}$ are hydrogen atom(s) or fluorine atom(s) simultaneously, ⋯⋯ is single bond or double bond wherein when $R^{2J}$ is fluorine atom, $A^J$ is only benzene, a salt thereof, an N-oxide thereof or a solvate thereof, or a prodrug thereof, or a cyclodextrin clathrate thereof.

(K) In the pamphlet of WO02/042268, it is described that the compound represented by the following formula (IK) has $EP_4$ agonistic activity. As well, the definition of each group of the compound represented by formula (IK) is described in the pamphlet of WO02/042268 in detail. Accordingly, $EP_4$ agonist of the present invention includes the compound represented by formula (IK):

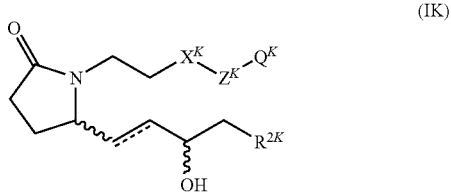

wherein the dotted line is a bond or no bond,
$X^K$ is —$CH_2$— or —O—,
$Z^K$ is —$(CH_2)_3$—, thienyl, thiazolyl or phenyl, provided that $X^K$ is O, then $Z^K$ is phenyl,
$Q^K$ is carboxy, C1-4 alkoxycarbonyl or tetrazolyl,
$R^{2K}$ is —$Ar^K$ or —$Ar^{1K}$—$V^K$—$Ar^{2K}$—,
$V^K$ is a bond, —O—, —$OCH_2$— or —$CH_2O$—,
$Ar^K$ is partially saturated, fully saturated or fully unsaturated 5 to 8 membered ring which may have 1 to 4 heteroatoms selected voluntarily from oxygen, sulfur and nitrogen, or bicyclic ring consisting of two fused partially saturated, fully saturated or fully unsaturated 5 to 6 membered rings which may have 1 to 4 heteroatoms selected voluntarily from oxygen, sulfur and oxygen, said partially or fully saturated ring or bicyclic ring optionally having 1 or 2 oxo groups substituted on carbon or 1 or 2 oxo groups substituted on sulfur, $Ar^{1K}$ and $Ar^{2K}$ are each independently a partially saturated, fully saturated or fully unsaturated 5 to 8 membered ring which may have 1 to 4 heteroatoms selected voluntarily from oxygen, sulfur or nitrogen, said partially or fully saturated ring optionally having one or two oxo groups substituted on carbon or 1 or 2 oxo groups substituted on sulfur, wherein the $Ar^K$ moiety may be substituted on carbon or nitrogen, on one ring if the moiety is monocyclic, or one or both rings if the moiety is bicyclic, with up to three substituents selected voluntarily from; (1) hydroxy, (2) a halogen atom, (3) carboxy, (4) C1-7 alkoxy, (5) C1-4 alkoxy C1-4 alkyl, (6) C1-7 alkyl, (7) C2-7 alkenyl, (8) C3-7 cycloalkyl, (9) C3-7 cycloalkyl C1-4 alkyl, (10) C3-7 cycloalkyl C1-4 alkanoyl, (11) formyl, (12) C1-8 alkanoyl, (13) C1-6 alkanoyl C1-4 alkyl, (14) C1-4 alkanoylamino, (15) C1-4 alkoxycarbonylamino, (16) hydroxysulfonyl, (17) aminocarbonylamino or mono-N-, di-N,N-, di-N,N'-, or tri-N,N,N'-aminocarbonyl substituted C1-4 alkyl, (18) sulfonamide, (19) C1-4 alkylsulfonamide, (20) amino, (21) mono-N- or di-N,N-C1-4 alkylamino, (22) carbamoyl, (23) mono-N- or di-N,N-C1-4 alkylcarbamoyl, (24) cyano, (25) thiol, (26) C1-6 alkylthio, (27) C1-6 alkylsulfinyl, (28) C1-4 alkylsulfonyl, (29) mono-N- or di-N,N-C1-4 alkylaminosulfinyl, wherein said alkyl and alkoxy substituents in the definition of $Ar^K$ are optionally substituted on carbon with up to three fluorine atom, wherein the $Ar^{1K}$ and $Ar^{2K}$ moieties may be substituted on carbon or nitrogen with up to three substituents selected from; (1) hydroxy, (2) a halogen atom, (3) carboxy, (4) C1-7 alkoxy, (5) C1-4 alkoxy C1-4 alkyl, (6) C1-7 alkyl, (7) C2-7 alkenyl, (8) C3-7 cycloalkyl, (9) C3-7 cycloalkyl C1-4 alkyl, (10) C3-7 cycloalkyl C1-4 alkanoyl, (11) formyl, (12) C1-8 alkanoyl, (13) C1-6 alkanoyl C1-4 alkyl, (14) C1-4 alkanoylamino, (15) C1-4 alkoxycarbonylamino, (16) hydroxysulfonyl, (17) aminocarbonylamino or mono-N-, di-N,N-, di-N,N'-, or tri-N,N,N'-aminocarbonyl substituted C1-4 alkyl, (18) sulfonamide, (19) C1-4 alkylsulfonamide, (20) amino, (21) mono-N- or di-N,N-C1-4 alkylamino, (22) carbamoyl, (23) mono-N- or di-N,N-C1-4 alkylcarbamoyl, (24) cyano, (25) thiol, (26) C1-6 alkylthio, (27) C1-6 alkylsulfinyl, (28) C1-4 alkylsulfonyl, (29) mono-N- or di-N,N-C1-4 alkylaminosulfinyl, wherein said alkyl and alkoxy substituents in the definition of $Ar^{1K}$ and $Ar^{2K}$ are optionally substituted on carbon with up to three fluorine atom, wherein (a) when $X^K$ is —$(CH_2)$— and $Z^K$ is —$(CH_2)_3$—, $R^{2K}$ is not thienyl, phenyl or phenyl monosubstituted with chlorine, fluorine, phenyl, methoxy, trifluoromethoxy or C1-4 alkyl, (b) when $X^K$ is —$(CH_2)$—, $Z^K$ is —$(CH_2)_3$—, and $Q^K$ is carboxy or C1-4 alkoxycarbonyl, $R^{2K}$ is not (i) C5-7 cycloalkyl or (ii) phenyl, thienyl or furyl each of which may be optionally monosubstituted or disubstituted by one or two substituents selected from (1) a halogen atom or (2) C1-3 alkyl which may be substituted by one or more halogen atom(s) or C1-4 alkoxy, a salt thereof, an N-oxide thereof or a solvate thereof, or a prodrug thereof, or a cyclodextrin clathrate thereof.

(L) In the pamphlet of WO03/008377, it is described that the compound represented by the following formula (IL) has $EP_4$ agonistic activity. As well, the definition of each group of the compound represented by formula (IL) is described in the pamphlet of WO03/008377 in detail. Accordingly, $EP_4$ agonist of the present invention includes the compound represented by formula (IL):

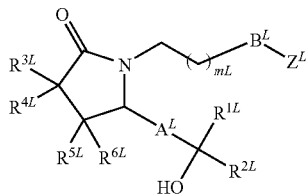

wherein $A^L$ is —$CH_2$—$CH_2$— or —CH=CH—, $B^L$ is a single bond, aryl or heteroary, $Z^L$ is —C(O)$OR^{\prime L}$, —C(O)$NR^{\prime L}R^{\prime\prime L}$, —C(O)$NSO_2R^{\prime L}$, —$PR^{\prime L}$(O)($OR^{\prime L}$), —PO($OR^{\prime L})_2$ or tetrazol-5-yl wherein $R^{\prime L}$ and $R^{\prime\prime L}$ are each independently hydrogen atom or C1-6 alkyl, mL is 1, 2, 3, 4, 5 or 6, $R^{1L}$ is alkyl, alkenyl, alkynyl, cycloalkylalkyl, heterocyclylalkyl, aryl, arylalkyl, heteroaryl, when $B^L$ is aryl or heteroaryl and $R^{3L}$, $R^{4L}$, $R^{5L}$ and $R^{6L}$ are not simultaneously a hydrogen atom, or $R^{1L}$ is heterocyclylalkyl, aryl, arylalkyl, heteroaryl, when $B^L$ is single bond and $R^{3L}$, $R^{4L}$, $R^{5L}$ and $R^{6L}$ are simultaneously hydrogen atom, $R^{2L}$ is a hydrogen atom, C1-6 alkyl, C1-6 alkenyl or C1-6 alkynyl, $R^{3L}$, $R^{4L}$, $R^{5L}$ and $R^{6L}$ are each independently hydrogen atom or C1-6 alkyl, $R^{3L}$ and $R^{4L}$, $R^{5L}$ and $R^{6L}$ or $R^{3L}$ and $R^{5L}$ taken together with the atom to which they are attached may form C3-7 alkyl ring, a salt thereof, an N-oxide thereof or a solvate thereof, or a prodrug thereof, or a cyclodextrin clathrate thereof.

(M) In the pamphlet of WO03/035064, it is described that the compound represented by the following formula (IM) binds to $EP_4$. As well, the definition of each group of the compound represented by formula (IM) is described in the pamphlet of WO03/035064 in detail. Accordingly, $EP_4$ agonist of the present invention includes the compound represented by formula (IM):

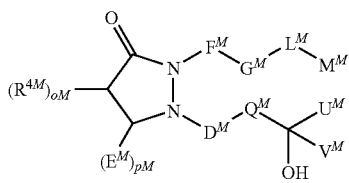

wherein each $R^{4M}$ is independently a hydrogen atom, alkyl which may be substituted, carbocyclic aryl which may be substituted or heteroaromatic which may be substituted, $E^M$ is a hydrogen atom, hydroxyl, optionally substituted alkoxy or optionally substituted alkylthio, oM and pM are each independently 0, 1 or 2, the sum of oM and pM is at least 1, $F^M$ is —$(CH_2)_{nM}$ wherein nM is an integer of from 1 to 6, $G^M$ is —C≡C—, —CH=CH—, —$CH_2$—, carbocyclic aryl which may be substituted or heteroaromatic which may be substituted, $L^M$ is $(CH_2)_{n'M}$ wherein n'M is an integer of from 0 to 3, $M^M$ is $COX^M$, $SO_2X^M$ wherein $X^M$ is $OR^{\prime M}$ or $NHR^{\prime M}$, $R^{\prime M}$ is H or optionally substituted alkyl, tetrazol which may be substituted, $NO_2$, $NHSO_2R^M$ or $NHC(O)R^M$ wherein $R^M$ is H, alkyl which may be substituted, $D^M$ is $(CH_2)_{n''M}$ wherein n"M is an integer of from 0 to 2, $Q^M$ is $(CH_2)_{n'''M}$ (wherein n'''M is 0 or 1), —CH=CH— or carbocyclic aryl which may be substituted, preferably phenyl which may be substituted, $U^M$ and $V^M$ are each independently alkyl which may be substituted, alkenyl which may be substituted, alkynyl which may be substituted, carbocyclic aryl which may be substituted, or heteroaromatic which may be substituted wherein the compound wherein $G^M$ is $CH_2$, $n^M$ is 3, $E^M$ is hydrogen atom and pM is 2, $R4^M$ is hydrogen atom and oM is 2, n"M is 2, n'''M is 0, $V^M$ is alkyl, is excepted, a salt thereof, an N-oxide thereof or a solvate thereof, a prodrug thereof, or a cyclodextrin clathrate thereof.

(N) In the pamphlet of WO03/053923, it is described that the compound represented by the following formula (IN) binds to $EP_4$. As well, the definition of each group of the compound represented by formula (IN) is described in the pamphlet of WO03/053923 in detail. Accordingly, $EP_4$ agonist of the present invention includes the compound represented by formula (IN):

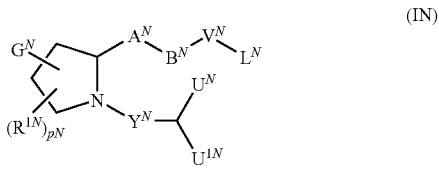

wherein, $R^{1N}$ is each independently a hydrogen atom, alkyl which may be substituted, alkenyl which may be substituted, alkynyl which may be substituted, heteroalkyl which may be substituted, heteroalkenyl which may be substituted, heteroalkynyl which may be substituted, carbocyclic aryl which may be substituted, aralkyl which may be substituted, heteroalicyclic which may be substituted, heteroaryl which may be substituted, heteroarylalkyl which may be substituted or heteroalicyclicalkyl which may be substituted, $G^N$ is oxo, a halogen atom, alkyl which may be substituted, alkoxy, hydroxyl or carboxylate which may be substituted, alkylcarboxylate ester which may be substituted, $P^N$ is an integer of from 0 to 4, $Y^N$ is $(CR^{2N}R^{3N})_{qN}$ which may include 0 or 1 C=C double bond wherein qN is an integer of from 1 to 6, $R^{2N}$ and $R^{3N}$ are each independently a hydrogen atom, substituted alkyl which may be substituted, alkenyl which may be substituted, alkynyl which may be substituted, hydroxyl, halogen atom, or alkoxy which may be substituted), $U^N$ and $U^{1N}$ are each independently a hydrogen atom, hydroxyl or alkyl which may be substituted, $A^N$ is O, S, $(CR^{2N}R^{3N})_{q'N}$ wherein, q'N is an integer of from 1 to 6, $B^N$ is $(CR^{2N}R^{3N})_{nN}$ or a single bond, $A^N$ and $B^N$ take together to form 1,2-vinylene or ethynylene which may be substituted, $V^N$ is $(CR^{2N}R^{3N})_{mN}$, divalent aryl which may be substituted or divalent heteroary which may be substituted, $L^N$ is C(O)$Z^N$, $Z^N$ is hydroxyl, alkyl which may be substituted, alkenyl which may be substituted, alkynyl which may be substituted, heteroalkyl which may be substituted, heteroalkenyl which may be substituted, heteroalkynyl which may be substituted, amino, $NR^{4N}R^{5N}$, cycloalkyl which may be substituted, heterocycloalkyl which may be substituted, carbocyclic aryl which may be substituted, heteroaryl which may be substituted, arylalkyl which may be substituted or heteroarylalkyl which may be substituted, nN is an integer of from 0 to 3, mN is an integer of from 1 to 6, $R^{4N}$ and $R^{5N}$ are each independently a hydrogen atom, alkyl which may be substituted, cycloalkyl which may be substituted, heterocycloalkyl which may be substituted, alkenyl which may be substituted, alkynyl which may be substituted, heteroalkyl which may be substituted, heteroalkenyl which may be substituted, heteroalkynyl which may be substituted, carbocyclic aryl which may be substituted, heteroaryl which may be substituted, arylalkyl which may be substituted or heteroarylalkyl which may be substituted, or $R^{4N}$ and $R^{5N}$ take together to be heterocycloalkyl], a salt thereof, an N-oxide thereof or a solvate thereof, or a prodrug thereof, or a cyclodextrin clathrate thereof.

(P) In the pamphlet of WO03/103664, it is described that the compound represented by the following formula (IP) has $EP_4$ agonistic activity. As well, the definition of each group of the compound represented by formula (IP) is described in the pamphlet of WO03/103664 in detail. Accordingly, $EP_4$ agonist of the present invention includes the compound represented by formula (IP):

(IP)

wherein $X^P$ is a single bond, an oxygen atom or a sulfur atom, $Y^P$ is =O or —OH, $R^{1P}$ is hydroxyl, CN, $(CH_2)_{pP}CO_2R^{6P}$, $(CH_2)_{nP}SO_3R^{6P}$, —$CF_2SO_2NH_2$, —$SO_2NH_2$, —$CHNHSO_2R^{2P}$—, —$SO_2NHCOR^{6P}$, —$PO(OH)_2$, $CONHPO_2R^{6P}$, $CONHR^{8P}$, C1-4 alkoxy, —$(CH_2)_{nP}NR^{6P}R^{7P}$, hydroxymethylketone or —$(CH_2)_{nP}$heterocyclyl, said heterocyclyl unsubstituted or substituted with 1 to 3 $R^{aP}$ and optionally containing an acidic hydrogen atom, $R^{2P}$ is hydrogen atom, C6-10 aryl or C1-4 alkyl, $R^{3P}$ and $R^{4P}$ are each independently a hydrogen atom, a halogen atom or C1-6 alkyl, $R^{5P}$ is $(CH_2)_{mP}$C6-10aryl, $(CH_2)_{mP}$C5-10heteroaryl, $(CH_2)_{mP}$C3-10heterocycloalkyl or $(CH_2)_{mP}$C3-10cycloalkyl, said cycloalkyl, heterocycloalkyl, aryl or heteroaryl unsubstituted or substituted with 1 to 3 $R^{aP}$, $R^{6P}$ and $R^{7P}$ are hydrogen atom or C1-4 alkyl, $R^{8P}$ is a hydrogen atom or sulfonyl, $Z^P$ is $(C(R^{bP})_2)_{nP}$, $R^{bP}$ is independently a hydrogen atom, a halogen atom, C1-6 alkyl or C3-6 cycloalkyl, $R^{aP}$ is C1-6 alkoxy, C1-6 alkyl, $CF_3$, nitro, amino, cyano, C1-6 alkylamino or a halogen atom, ----- is a double bond or single bond, pP is 1 to 3, nP is 0 to 4, mP is 0 to 8, a salt thereof, an N-oxide thereof or a solvate thereof, or a prodrug thereof, or a cyclodextrin clathrate thereof.

(Q) In the pamphlet of WO03/007941, it is described that the compound represented by the following formula (IQ) has $EP_4$ agonistic activity. As well, the definition of each group of the compound represented by formula (IQ) is described in the pamphlet of WO03/007941 in detail. Accordingly, $EP_4$ agonist of the present invention includes the compound represented by formula (IQ):

(IQ)

wherein $Q^Q$ is $CH_2$, an oxygen atom, $B^Q$ is —$CH_2$—, —$(CH_2)_2$—, —$(CH_2)_3$—, —$(CH_2)_4$—, —$(CH_2)_5$—, —CH=CH—, —$CH_2$—CH=CH—, —CH=CH—$CH_2$— or —$CH_2$—CH=CH—$CH_2$—, provided that when $B^Q$ is —CH=CH—, or —CH=CH—$CH_2$—, then $Q^Q$ is $CH_2$, $X^Q$ is —$NR^{aQ}$— wherein $R^{aQ}$ is a hydrogen atom, a halogen atom, C1-6 alkyl, C1-6 acyl, —O—, —S—, —SO—, —$SO_2$— or a single bond, wherein $X^Q$ is a single bond, then $Q^Q$ is an oxygen atom, $J^Q$ is —$(CR^{bQ}R^{cQ})_{nQ}$— wherein nQ is an integer of from 1 to 4, $R^{bQ}$ and $R^{cQ}$ are both hydrogen atom, or one or two of $R^{bQ}$ and $R^{cQ}$ are lower alkyl and the remainder is hydrogen atom, or $R^{bQ}$ and $R^{cQ}$ if attached to the same carbon atom form a C2-5 polymethylene, or —$CH_2$—CH=CH—, $A^Q$ is —$CH_2$—$CH_2$—, —CH=CH— or —C≡C—, $Z^Q$ is $CH_2OH$, —$C(O)OR^{1Q}$, —$C(O)NR'^QR''^Q$, —$C(O)NSO_2R'^Q$, —$P(C1-6\ alkyl)(O)(OR'^Q)$, —$PO(OR'^Q)_2$ or tetrazol-5-yl wherein $R'^Q$ and $R''^Q$ are each independently hydrogen atom or C1-6 alkyl, nQ is 1, 2, 3 or 4, $R^{1Q}$ is —$(CH_2)_{pQ}R^{7Q}$ or —$(CH_2)_{qQ}OR^{8Q}$ wherein $R^{7Q}$ and $R^{8Q}$ are each independently C1-6 alkyl, halo C1-6 alkyl, C3-6 cycloalkyl, heterocyclyl, aryl or heteroaryl, pQ and qQ are each independently 0, 1, 2, 3, 4 or 5, $R^{2Q}$ is a hydrogen atom, C1-6 alkyl, C1-6 alkenyl, C1-6 alkynyl, $R^{3Q}$, $R^{4Q}$, $R^{5Q}$ and $R^{6Q}$ are each independently hydrogen atom or C1-6 alkyl, a salt thereof, an N-oxide thereof or a solvate thereof, or a prodrug thereof, or a cyclodextrin clathrate thereof.

(R) In the pamphlet of WO03/074483, it is described that the compound represented by the following formula (IR) has $EP_4$ agonistic activity. As well, the definition of each group of the compound represented by formula (IR) is described in the pamphlet of WO03/074483 in detail. Accordingly, $EP_4$ agonist of the present invention includes the compound represented by formula (IR):

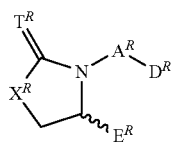
(IR)

wherein $T^R$ is (1) an oxygen atom, or (2) a sulfur atom,
$X^R$ is (1) —CH$_2$—, (2) —O—, or (3) —S—,
$A^R$ is $A^{1R}$ or $A^{2R}$,
$A^{1R}$ is (1) C2-8 straight chain alkylene which may be substituted by 1 or 2 C1-4 alkyl, (2) C2-8 straight chain alkenylene which may be substituted by 1 or 2 C1-4 alkyl, or (3) C2-8 straight chain alkynylene which may be substituted by 1 or 2 C1-4 alkyl,
$A^{2R}$ is -$G^{1R}$-$G^{2R}$-$G^{3R}$,
$G^{1R}$ is (1) C1-4 straight chain alkylene which may be substituted by 1 or 2 C1-4 alkyl, (2) C2-4 straight chain alkenylene which may be substituted by 1 or 2 C1-4 alkyl, (3) C2-4 straight chain alkynylene which may be substituted by 1 or 2 C1-4 alkyl,
$G^{2R}$ is (1) —$Y^R$—, (2) -ring$1^R$-, (3) —$Y^R$-ring$^{1R}$-, (4) -ring$^{1R}$-$Y^R$—, or (5) —$Y^R$—C1-4alkylene-ring$^{1R}$-,
$Y^R$ is (1) —S—, (2) —SO—, (3) —SO$_2$—, (4) —O—, or (5) —NR$^{1R}$—,
$R^{1R}$ is (1) a hydrogen atom, (2) C1-10 alkyl, or (3) C2-10 acyl,
$G^{3R}$ is (1) bond, (2) C1-4 straight chain alkylene which may be substituted by 1 or 2 C1-4 alkyl, (3) C2-4 straight chain alkenylene which may be substituted by 1 or 2 C1-4 alkyl, or (4) C2-4 straight chain alkynylene which may be substituted by 1 or 2 C1-4 alkyl,
$D^R$ is $D^{1R}$ or $D^{2R}$,
$D^{1R}$ is (1) —COOH, (2) —COOR$^{2R}$, (3) tetrazol-5-yl, or (4) —CONR$^{3R}$SO$_2$R$^{4R}$,
$R^{2R}$ is (1) C1-10 alkyl, (2) phenyl, (3) C1-10 alkyl substituted by phenyl, or (4) biphenyl,
$R^{3R}$ is (1) a hydrogen atom, or (2) C1-10 alkyl,
$R^{4R}$ is (1) C1-10 alkyl, or (2) phenyl,
$D^{2R}$ is (1) —CH$_2$OH, (2) —CH$_2$OR$^{5R}$, (3) hydroxy, (4) —OR$^{5R}$, (5) formyl, (6) —CONR$^{6R}$R$^{7R}$, (7) —CONR$^{6R}$SO$_2$R$^{8R}$, (8) —CO—(NH-amino acid residue-CO)$_{mR}$—OH, (9) —O—(CO-amino acid residue-NH)$_{mR}$—H, (10) —COOR$^{9R}$, (11) —OCO—R$^{10R}$, (12) —COO—Z$^{1R}$-Z$^{2R}$-Z$^{3R}$, or

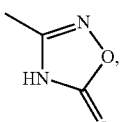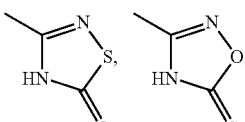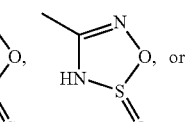 (13)

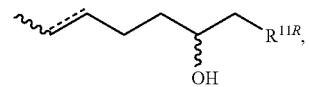

$R^{5R}$ is C1-10 alkyl,
$R^{6R}$ and $R^{7R}$ are each independently (1) a hydrogen atom, or (2) C1-10 alkyl,
$R^{8R}$ is C1-10 alkyl substituted by phenyl,
$R^{9R}$ is (1) C1-10 alkyl substituted by biphenyl which may be substituted by 1 to 3 substituents selected from C1-10 alkyl, C1-10 alkoxy and a halogen atom, or (2) biphenyl substituted by 1 to 3 substituents selected from C1-10 alkyl, C1-10 alkoxy, and a halogen atom,
$R^{10R}$ is (1) phenyl, or (2) C1-10 alkyl,
mR is 1 or 2,
$Z^{1R}$ is (1) C1-15 alkylene, (2) C2-15 alkenlylene, or (3) C2-15 alkynylene,
$Z^{2R}$ is (1) —CO—, (2) —OCO—, (3) —COO—, (4) —CONR$^{Z1R}$—, (5) —NR$^{Z2R}$CO—, (6) —O—, (7) —S—, (8) —SO$_2$—, (9) —SO$_2$—NR$^{Z2R}$—, (10) —NR$^{Z2R}$SO$_2$—, (11) —NR$^{Z3R}$—, (12) —NR$^{Z4R}$CONR$^{Z5R}$—, (13) —NR$^{Z6R}$COO—, (14) —OCONR$^{Z7R}$—, or (15) —OCOO—, $Z^{3R}$ is (1) hydrogen atom, (2) C1-15 alkyl, (3) C2-15 alkenyl, (4) C2-15 alkynyl, (5) ringZ$^R$, or (6) C1-10 alkoxy, C1-10 alkylthio, C1-10 alkyl-NR$^{Z8R}$— or C1-10 alkyl substituted by ringZ$^R$,
ringZ$^R$ is (1) optionally or fully saturated C3-15 mono-, bi-, tri-carbocyclic aryl or (2) optionally or fully saturated 3-15 membered mono-, bi-, tri-heterocyclic aryl containing 1-4 hetero atoms selected from oxygen atom, nitrogen atom, and sulfur atom,
$R^{Z1R}$, $R^{Z2R}$, $R^{Z3R}$, $R^{Z4R}$, $R^{Z5R}$, $R^{Z6R}$, $R^{Z7R}$ and $R^{Z8R}$ are each independently hydrogen atom or C1-15 alkyl,
$R^{Z1R}$ and $Z^{3R}$ taken together with the nitrogen atom which they attached may be 5-7 membered saturated mono-heterocyclic ring, the above described heterocyclic ring may further contain one hetero atom selected from oxygen atom, nitrogen atom and sulfur atom,
RingZ$^R$ and the saturated mono-heterocyclic ring formed by $R^{Z1R}$ and $Z^{3R}$ and the nitrogen atom to which they are attached may be substituted by 1 to 3 groups selected from following (1) to (4); (1) C1-15 alkyl, (2) C2-15 alkenyl, (3) C2-15 alkynyl, (4) C1-10 alkyl substituted by C1-10 alkoxy, C1-10 alkylthio, or C1-10 alkyl-NR$^{Z9R}$—;
$R^{Z9R}$ is hydrogen atom, or C1-10 alkyl,
$E^R$ is $E^{1R}$ or $E^{2R}$,
$E^R$ is

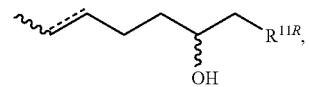

$R^{11R}$ is (1) C1-10 alkyl, (2) C1-10 alkylthio, (3) C1-10 alkyl substituted by C3-8 cycloalkyl, (4) C1-10 alkyl substituted by ring$2^R$, or (5) C1-10 alkyl substituted by —W$^{1R}$—W$^{2R}$-ring$2^R$,
$W^{1R}$ is (1) —O—, (2) —S—, (3) —SO—, (4) —SO$_2$—, (5) —NR$^{11-1R}$—, (6) carbonyl, (7) —NR$^{11-1R}$SO$_2$—, (8) carbonylamino, or (9) aminocarbonyl,
$R^{11-1R}$ is (1) a hydrogen atom, (2) C1-10 alkyl, or (3) C2-10 acyl,
$W^{2R}$ is (1) a bond, or (2) C1-8 alkyl substituted by C1-4 alkyl, a halogen atom, or hydroxy,
$E^{2R}$ is (1) U$^{1R}$—U$^{2R}$—U$^{3R}$, or (2) ring$4^R$,
$U^{1R}$ is (1) C1-4 alkylene, (2) C2-4 alkenylene, (3) C2-4 alkynylene, (4) -ring$3^R$—, (5) C1-4 alkylene-ring$3^R$—, (6) C2-4 alkenylene-ring$3^R$—, or (7) C2-4 alkynylene-ring$3^R$—,
$U^{2R}$ is (1) a bond, (2) —CH$_2$—, (3) —CHOH—, (4) —O—, (5) —S—, (6) —SO—, (7) —SO$_2$—, (8) —NR$^{12R}$—, (9) carbonyl, (10) —NR$^{12R}$SO$_2$—, (11) carbonylamino, or (12) aminocarbonyl,
$R^{12R}$ is (1) a hydrogen atom, (2) C1-10 alkyl, or (3) C2-10 acyl,
$U^{3R}$ is (1) C1-8 alkyl optionally substituted by 1 to 3 substituents selected from C1-10 alkyl, a halogen atom, hydroxyl, alkoxy, alkylthio, and $NR^{13R}R^{14R}$, (2) C2-8 alkenyl which may be substituted by 1 to 3 substituents selected from C1-10 alkyl, a halogen atom, hydroxyl, alkoxy, alkylthio, and $NR^{13R}R^{14R}$, (3) C2-8 alkynyl which may be substituted by 1 to 3 substituents selected from C1-10 alkyl, a halogen atom, hydroxyl, alkoxy, alkylthio, and $NR^{13R}R^{14R}$, (4) C1-8 alkyl substituted by ring4$^R$, or (5) ring4$^R$, $R^{13R}$ and $R^{14R}$ are each independently (1) hydrogen atom, or (2) C1-10 alkyl, ring1$^R$, ring2$^R$, ring3$^R$, or ring4$^R$ may be substituted by 1 to 5 $R^R$, $R^R$ is (1) C1-10 alkyl, (2) C2-10 alkenyl, (3) C2-10 alkynyl, (4) C1-10 alkoxy, (5) C1-10 alkylthio, (6) a halogen atom, (7) hydroxy, (8) nitro, (9) —$NR^{15R}R^{16R}$, (10) C1-10 alkyl substituted by C1-10 alkoxy, (11) C1-10 alkyl substituted by 1 to 3 halogen atoms, (12) C1-10 alkyl substituted by C1-10 alkoxy substituted by 1 to 3 halogen atoms, (13) C1-10 alkyl substituted by —$NR^{15R}R^{16R}$, (14) ring5$^R$, (15) —O-ring5$^R$-, (16) C1-10 alkyl substituted by ring5$^R$, (17) C2-10 alkenyl substituted by ring5$^R$, (18) C2-10 alkynyl substituted by ring5$^R$, (19) C1-10 alkoxy substituted by ring5$^R$, (20) C1-10 alkyl substituted by —O-ring5$^R$, (21) $COOR^{17R}$, (22) C1-10 alkoxy substituted by 1 to 4 halogen atoms, (23) formyl, (24) C1-10 alkyl substituted by hydroxyl, or (25) C2-10 acyl, $R^{15R}$, $R^{16R}$, and $R^{17R}$ are each independently (1) a hydrogen atom, or (2) C1-10 alkyl, ring5$^R$ may be substituted by 1 to 3 substituents selected from following (1) to (9);

(1) C1-10 alkyl, (2) C2-10 alkenyl, (3) C2-10 alkynyl, (4) C1-10 alkoxy, (5) C1-10 alkyl substituted by C1-10 alkoxy, (6) halogen atom, (7) hydroxyl, (8) C1-10 alkyl substituted by 1 to 3 halogen atoms, (9) C1-10 alkyl substituted by C1-10 alkoxy substituted by 1 to 3 halogen atoms;

ring1$^R$, ring2$^R$, ring3$^R$, ring4$^R$ and ring5$^R$ are each independently, (1) C3 to 15 mono-, bi- or tri-carbocyclic aryl which may be partially or fully saturated or (2) 3 to 15 membered mono-, bi- or tri-heterocyclic aryl containing hetero atoms selected from 1 to 4 nitrogen atom(s), 1 to 2 oxygen atom(s) and/or 1 to 2 sulfur atom(s) which may be partially or fully saturated wherein 1) when $E^R$ is $E^{2R}$, $E^{2R}$ is $U^{1R}$—$U^{2R}$—$U^{3R}$, and $U^{1R}$ is C2 alkylene or C2 alkenylene, $U^{2R}$ is not —CHOH—, 2) when $U^{3R}$ is C1-8 alkyl substituted by at least one hydroxyl, $U^{1R}$—$U^{2R}$ is neither C2 alkylene nor C2 alkenylene, 3) when $A^R$ is $A^{1R}$ and $D^R$ is $D^{1R}$, $E^R$ is not $E^{1R}$, 4) when $T^R$ is oxygen atom, $X^R$ is —CH$_2$—, $D^R$ is $D^{1R}$, $D^{1R}$ is COOH, $A^R$ is $A^{1R}$, $A^{1R}$ is straight chain C2-8 alkylene, $E^R$ is $E^{2R}$, $E^{2R}$ is $U^{1R}$—$U^{2R}$—$U^{3R}$, $U^{1R}$ is C1-4 alkylene, and $U^{3R}$ is C1-8 alkyl, $U^{2R}$ is neither bond, —CH$_2$—, $NR^{12R}$—, nor carbonyl, 5) when $T^R$ is oxygen atom, $X^R$ is CH$_2$—, $D^R$ is $D^{1R}$, $D^{1R}$ is COOH, $A^R$ is $A^{2R}$, $G^{1R}$ is C1-4 alkylene, $G^{2R}$ is —O— or —$NR^{1R}$—, $G^{3R}$ is bond or C1-4 alkylene, $E^R$ is $E^{2R}$, $E^{2R}$ is $U^{1R}$—$U^{2R}$—$U^{3R}$, $U^{1R}$ is C1-4 alkylene and $U^{3R}$ is C1-8 alkyl, then $U^{2R}$ is not bond, —CH$_2$—, —$NR^{12R}$—, or carbonyl, 6) when $T^R$ is an oxygen atom, $X^R$ is —CH$_2$—, $D^R$ is $D^{1R}$, $E^R$ is $E^{2R}$, $E^{2R}$ is $U^{1R}$—$U^{2R}$—$U^{3R}$, $U^{1R}$ is C2 alkylene or C2 alkenylene and $U^{2R}$ is —CO—, then $A^R$ is not $A^{1R}$, 7) 4-[(2-{(2R)-2-[(1E,3S)-3-hydroxy-oct-1-enyl]-5-oxo-pyrrolidin-1-yl}ethyl)thio]butanoic acid and 4-{2-[(R)-2-((E)-3-hydroxy-oct-1-enyl)-5-oxo-pyrrolidin-1-yl]-ethyl}-benzoic acid are excluded), a salt thereof, an N-oxide thereof or a solvate thereof, or a prodrug thereof, or a cyclodextrin clathrate thereof.

(S) In the pamphlet of US2005/0049227, it is described that the compound represented by the following formula (IS) has EP$_4$ agonistic activity. As well, the definition of each group of the compound represented by formula (IS) is described in the pamphlet of US2005/0049227 in detail. Accordingly, EP$_4$ agonist of the present invention includes the compound represented by formula (IS):

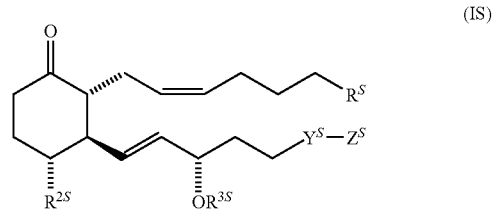

(IS)

wherein $R^S$ is $CO_2R^{4S}$, $CONR^{4S}{}_2$, $CH_2OR^{4S}$, $CONR^{4S}SO_2R^{4S}$, $P(O)(OR^{4S})$,

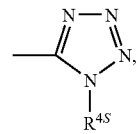

$R^{4S}$ is hydrogen atom, phenyl, C1-6 alkyl, $R^{1S}$ and $R^{2S}$ are each independently a hydrogen atom, hydroxyl, C1-6 alkyloxy, C1-6 acyloxy, $R^{3S}$ is a hydrogen atom, C1-6 alkyl, C1-6 acyl, $Y^S$ is bond, or —CH$_2$—, —O—, —S—, —N—, $Z^S$ is C3-10 alkyl, C3-10 cycloalkyl, 6 to 10 membered aromatic carbocyclic ring, 4 to 10 membered aromatic heterocyclic ring containing one hetero atom selected from nitrogen atom, oxygen atom and sulfur atom, a salt thereof, an N-oxide thereof or a solvate thereof, or a prodrug thereof, or a cyclodextrin clathrate thereof.

(T) In the pamphlet of WO2004/085430, it is described that the compound represented by the following formula (IT) has EP$_4$ agonistic activity. As well, the definition of each group of the compound represented by formula (IT) is described in the pamphlet of WO2004/085430 in detail. Accordingly, EP$_4$ agonist of the present invention includes the compound represented by formula (IT):

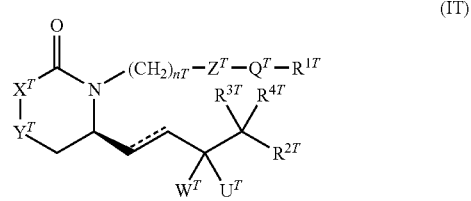

(IT)

wherein $Q^T$ is $(CH_2)_{mT}$, $(CH_2)_{mT}$—C6-10 aryl, $(CH_2)_{mT}$—C5-10 heterocyclic ring, $(CH_2)_{mT}$—C3-10 heterocyclic alkyl, $(CH_2)_{mT}$—C3-8 cycloalkyl, methylene substituted by two halogen atoms, said cycloalkyl, heterocyclic alkyl, aryl, or a heterocyclic ring may be substituted by three $R_{aT}$, $X^T$ and $Y^T$ are each independently methylene, an oxygen atom, a nitrogen atom substituted by $R^{9T}$, a sulfur atom, wherein, $X^T$ and $Y^T$ are not an oxygen atom, a nitrogen atom substituted by $R^{9T}$, or a sulfur atom at the same time, $U^T$ is a hydrogen atom, C1-3 alkyl, or is not present when $W^T$ is oxo, $W^T$ is hydroxyl, oxo, provided that UT is not present when $W^T$ is oxo, $R^{1T}$ is $-(CH_2)_{pT}$-hydroxyl, $-(CH_2)_{pT}$-cyano, $-(CH_2)_{pT}-CO_2R^{10T}$, $-(CH_2)_{nT}-SO_3R^{6T}$, $-(CH_2)_{pT}-CF_2SO_2NH_2$, $-(CH_2)_{pT}-SO_2NH_2$, $-(CH_2)_{pT}-CONHSO_2R^{2T}$, $-(CH_2)_{pT}-SO_2NHCOR^{2T}$, $-(CH_2)_{pT}-PO(OH)_2$, $(CH_2)_{pT}-CONHPO_2R^{6T}$, $-(CH_2)_{pT}-CONHR^{8T}$, $-(CH_2)_{pT}-C1$-4 alkoxy, $-(CH_2)_{pT}-$cycloalkyl, $-(CH_2)_{pT}$-hydroxymethylketone, $-(CH_2)_{nT}-$heterocyclic ring, said heterocyclic ring may be substituted by 1 to 3 $R^{aT}$ and optionally contains an acidic hydroxyl, $R^{2T}$ is independently C1-10 alkyl, $(CH_2)_{mT}-C6$-10 aryl, $(CH_2)_{mT}-C5$-10 heterocyclic ring, $(CH_2)_{mT}-C3$-10 heterocyclic alkyl, $(CH_2)_{mT}-C3$-8 cycloalkyl, O—C1-10 alkyl, O—C6-10 aryl, O—C3-10 cycloalkyl, O—C3-10 heterocyclic alkyl, provided that $R^{2T}$ is O—C1-10 alkyl, O—C6-10 aryl, O—C3-10 cycloalkyl, O—C3-10 heterocyclic alkyl, then $R^{3T}$ and $R^{4T}$ are not halogen atoms, said alkyl, cycloalkyl, heterocyclic alkyl, aryl, or a heterocyclic ring optionally substituted by 1 to 3 $R^{aT}$, $R^{3T}$ and $R^{4T}$ are each independently a hydrogen atom, a halogen atom, C1-6 alkyl, or $R^{3T}$ and $R^{4T}$ may be taken together to form a 3-7 membered carbocyclic ring optionally containing of 1 to 2 hetero atoms selected from an oxygen atom, sulfur atom, SO, $SO_2$ and a nitrogen atom substituted by $R^{9T}$ $R^{6T}$ and $R^{7T}$ are each independently hydrogen atom, C1-4 alkyl, $R^{8T}$ is a hydrogen atom, acyl, sulfonyl, $R^{9T}$ is a hydrogen atom, C1-6 alkyl, said alkyl optionally be substituted by 1 to 3 halogen atoms, cyano, hydroxyl, C1-6 alkoxy, C1-6 acyloxy, amino, $R^{10T}$ is a hydrogen atom, C1-10 alkyl, C3-10 cycloalkyl, $(CH_2)_{pT}-C6$-10 aryl, $(CH_2)_{pT}-C5$-10 heterocyclic ring, $CR^{6T}R^{7T}OC(O)-C3$-10 cycloalkyl, $CR^{6T}R^{7T}OC(O)-C1$-10 alkyl, $Z^T$ is a triple bond, an oxygen atom, a sulfur atom, $(C(R^{bT})_2)_{nT}$, $-CH=CH-$, $R^{bT}$ is a hydrogen atom, C1-6 alkyl, a halogen atom, $R^{aT}$ is C1-6 alkoxy, C1-6 alkyl, $CF_3$, nitro, amino, cyano, C1-6 alkylamino, halogen atom, $R^{aT}$ is further aryl, heterocyclic ring, S—C1-6 alkyl, S—C6-10 aryl, S—C5-10 heterocyclic ring, $CO_2R^{6T}$, O—C6-10 aryl, O—C5-10 heterocyclic ring, $CH_2O$—C1-6 alkyl, $CH_2S$—C1-6 alkyl, $CH_2O$-aryl, $CH_2S$-aryl, ===== is a double bond or single bond, pT is 0 to 3, nT is 0 to 4, mT is 0 to 8, a salt thereof, an N-oxide thereof or a solvate thereof, or a prodrug thereof, or a cyclodextrin clathrate thereof.

(U) In the pamphlet of WO2004/085431, it is described that the compound represented by the following formula (IU) has $EP_4$ agonistic activity. As well, the definition of each group of the compound represented by formula (IU) is described in the pamphlet of WO2004/085431 in detail. Accordingly, $EP_4$ agonist of the present invention includes the compound represented by formula (IU):

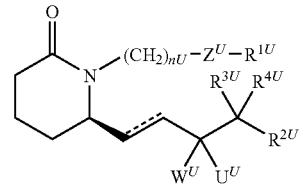

(IU)

wherein $U^U$ is a hydrogen atom, C1-3 alkyl, or is not present when $W^U$ is OXO, $W^U$ is hydroxyl, oxo, provided that, $U^U$ is not present when $W^U$ is oxo, $Z^U$ is $(CH_2)_{nU}$, $-CH=CH-$, $R^{1U}$ is $(CH_2)_{pU}$-hydroxyl, $(CH_2)_{pU}-CO_2R^{10U}$, $(CH_2)_{nU}$ heterocyclic ring, wherein the heterocyclic ring may be substituted by 1 to 3 $R^{aU}$ and may contain an acidic hydroxyl, $R^{2U}$ is independently C1-10 alkyl, $(CH_2)_{mU}-C6$-10 aryl, $(CH_2)_{mU}-C5$-10 heterocyclic ring, $(CH_2)_{mU}-C3$-10 heterocyclic alkyl, $(CH_2)_{mU}-C3$-8 cycloalkyl, said alkyl, cycloalkyl, heterocyclic alkyl, aryl, or heterocyclic ring may be substituted by 1 to 3 $R^{aU}$, $R^{3U}$ and $R^{4U}$ are each independently a hydrogen atom, a halogen atom, C1-6 alkyl, $R^{6U}$ is a hydrogen atom, C1-4 alkyl, $R^{10U}$ is a hydrogen atom, C1-10 alkyl, C3-10 cycloalkyl, $(CH_2)_{pU}-C6$-10 aryl, $(CH_2)_{pU}-C5$-10 heterocyclic ring, $R^{aU}$ is C1-6 alkoxy, C1-6 alkyl, $CF_3$, nitro, amino, cyano, C1-6 alkylamino, halogen atom, $R^{aU}$ is further aryl, a heterocyclic ring, S—C1-6 alkyl, S—C6-10 aryl, S—C5-10 heterocyclic ring, O—C6-10 aryl, O—C5-10 heterocyclic ring, $CO_2R^{6U}$, $CH_2O$—C1-6 alkyl, $CH_2S$—C1-6 alkyl, $CH_2O$-aryl, $CH_2S$-aryl, ===== is a double bond or single bond, pU is 0 to 3, nU is 0 to 4, mU is 0 to 8, a salt thereof, an N-oxide thereof or a solvate thereof, or a prod rug thereof, or a cyclodextrin clathrate thereof.

(W) In the pamphlet of WO2004/063158, it is described that the compound represented by the following formula (IW) has $EP_4$ agonistic activity. As well, the definition of each group of the compound represented by formula (IW) is described in the pamphlet of WO2004/063158 in detail. Accordingly, $EP_4$ agonist of the present invention includes the compound represented by formula (IW):

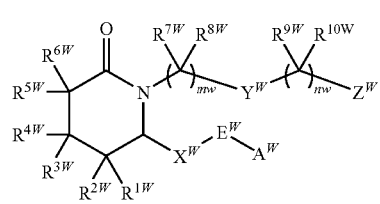

(IW)

wherein mW is 1 to 4, nW is 0 to 4, $A^W$ is alkyl, aryl, heteroaryl, arylalkyl, arylcycloalkyl, cycloalkylalkyl, aryloxyalkyl, $E^W$ is $-CHOH-$, $-C(O)-$, $X^W$ is $-(CH_2)_2-$, $-CH=CH-$, $Y^W$ is —$CH_2$—, —CH=CH—, arylene, heteroarylene, —O—, —$S(O)_{pW}$— wherein pW is 0 to 2, —$NR^{aW}$— wherein, $R^{aW}$ is hydrogen atom, alkyl, $Z^W$ is —$CH_2OH$—, —CHO, tetrazol-5-yl, —$COOR^{bW}$ wherein $R^{bW}$ is hydrogen atom, alkyl, $R^{1W}$, $R^{2W}$, $R^{3W}$, $R^{4W}$, $R^{5W}$, $R^{6W}$, $R^{7W}$, $R^{8W}$, $R^{9W}$ and $R^{10W}$ are each independently a hydrogen atom, alkyl, a salt thereof, an N-oxide thereof or a solvate thereof, or a prodrug thereof, or a cyclodextrin clathrate thereof.

As $EP_4$ agonist of the present invention, the compound represented by formula (I):

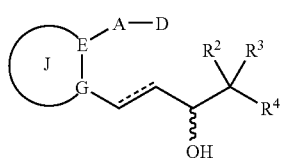

wherein all the symbols have the same meaning as mentioned above] is preferred, the compound represented by formula (IA) to (IW) more preferably is listed, the compound represented by formula (IA), (IB), (IQ) further preferably is listed.

As particularly preferably compound, a compound selected from
({3-[((1R,2S,3R)-3-hydroxy-2-{(1E,3S)-3-hydroxy-4-[3-(methoxymethyl)phenyl]but-1-enyl}-5-oxocyclopentyl)sulfanyl]propyl}sulfanyl)acetic acid;
4-{[2-((1R,2R,3R)-3-hydroxy-2-{(1E,3S)-3-hydroxy-4-[3-(methoxymethyl)phenyl]but-1-enyl}-5-oxocylcopentyl)ethyl]sulfanyl}butanoic acid;
7-((1R,2R,3R)-3-hydroxy-2-{(1E,3S)-3-hydroxy-4-[3-(methoxymethyl)phenyl]but-1-enyl}-5-oxocyclopentyl)heptanoic acid;
(5Z)-7-((1R,2R,3R)-2-{(1E,3S)-4-[3-(ethoxymethyl)phenyl]-3-hydroxybut-1-enyl}-3-hydroxy-5-oxocyclopentyl)hept-5-enoic acid;
(5Z)-7-((1R,2R,3R,5R)-5-chloro-2-{(1E,3S)-4-[3-(ethoxymethyl)phenyl]-3-hydroxybut-1-enyl}-3-hydroxycyclopentyl)hept-5-enoic acid;
4-[(2-{(1R,2R,3R)-3-hydroxy-2-[(1E,3S)-3-hydroxy-4-(4-hydroxy-3-methylphenyl)but-1-enyl]-5-oxocyclopentyl}ethyl)sulfanyl]butanoic acid;
methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate;
4-{[2-((1R,2R)-2-{(1E,3S)-3-hydroxy-4-[3-(methoxymethyl)phenyl]but-1-enyl}-5-oxocyclopentyl)ethyl]sulfanyl}butanoic acid;
4-[(2-{(2R)-2-[(1E,3S)-4-(3-chlorophenyl)-3-hydroxybut-1-enyl]-5-oxopyrrolidin-1-yl}ethyl)sulfanyl]butanoic acid;
4-{[2-((2R)-2-{(1E,3S)-3-hydroxy-4-[3-(trifluoromethyl)phenyl]but-1-enyl}-5-oxopyrrolidin-1-yl)ethyl]sulfanyl}butanoic acid;
4-[(2-{(2R)-2-[(1E,3S)-4-(4-fluorophenyl)-3-hydroxybut-1-enyl]-5-oxopyrrolidin-1-yl}ethyl)sulfanyl]butanoic acid;
4-[(2-{(2R)-2-[(1E,3S)-3-hydroxy-4-(2-naphthyl)-but-1-enyl]-5-oxopyrrolidin-1-yl}ethyl)sulfanyl]butanoic acid;
4-[(2-{(4S)-4-[(1E,3S)-4-(4-fluorophenyl)-3-hydroxy-1-butenyl]-2-oxo-1,3-oxazolidin-3-yl}ethyl)sulfanyl]butanoic acid;
2-[(2-{(2R)-2-[(1E,3S)-3-hydroxy-4-(3-methylphenyl)but-1-enyl]-5-oxopyrrolidin-1-yl}ethyl)sulfanyl]-1,3-thiazole-4-carboxylic acid;
2-[(2-{(2R)-2-[(1E,3S)-3-hydroxyoct-1-enyl]-5-oxopyrrolidin-1-yl}ethyl)sulfanyl]-1,3-thiazole-4-carboxylic acid;
2-{[2-((2R)-2-{(1E,3S)-4-[3-(1-benzofuran-2-yl)phenyl]-3-hydroxybut-1-enyl}-5-oxopyrrolidin-1-yl)ethyl]sulfanyl}-1,3-thiazole-4-carboxylic acid;
4-[(2-{(2R)-2-[(1E,3S)-3-hydroxyocat-1-enyl]-5-oxopyrrolidin-1-yl}ethyl)sulfanyl]butanoic acid;
{[3-({(1R,2S,3R)-3-hydroxy-2-[(1E,3S)-3-hydroxyoct-1-enyl]-5-oxocyclopentyl}sulfanyl)propyl]sulfanyl}acetic acid; and
2-[(2-{(4S)-4-[(1E,3S)-4-(4-fluorophenyl)-3-hydroxybut-1-enyl]-2-oxo-1,3-oxazolidin-3-yl}ethyl)sulfanyl]-1,3-thiazole-4-carboxylic acid, a salt thereof, a hydrate thereof or a prodrug thereof, or a cyclodextrin clathrate thereof is listed. As most preferably compound, a compound selected from
({3-[((1R,2S,3R)-3-hydroxy-2-{(1E,3S)-3-hydroxy-4-[3-(methoxymethyl)phenyl]but-1-enyl}-5-oxocyclopentyl)sulfanyl]propyl}sulfanyl)acetic acid,
methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate,
and 4-[(2-{(2R)-2-[(1E,3S)-4-(4-fluorophenyl)-3-hydroxybut-1-enyl]-5-oxopyrrolidin-1-yl}ethyl)sulfanyl]butanoic acid, a salt thereof, a hydrate thereof or a prodrug thereof, or a cyclodextrin clathrate thereof is listed.

[Isomer]

Unless otherwise specified, all isomers are included in the present invention. For example, alkyl, alkenyl, alkynyl, alkyloxy, alkoxy, alkenyloxy, alkynyloxy, alkylthio, alkylsulfinyl, alkylsulfonyl, alkylene, alkenylene, alkynylene, acyl and acyloxy group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention.

According to the present invention, unless otherwise indicated and as is apparent for those skilled in the art, the symbol ...ᐞ indicates that it is bound to the opposite side of the sheet (namely α-configuration), the symbol ⁄ indicates that it is bound to the front side of the sheet (namely β-configuration), the ⁓ indicates that it is a α-configuration, β-configuration or a mixture thereof which may be mixed by optional ratio, and the symbol ⁄ indicates that it is a mixture of α-configuration and β-configuration which may be mixed by optional ratio.

[Salt and Solvate]

The compounds represented by formula (I) can be converted into salts thereof by known methods. As salts, non-toxic, water-soluble salts are preferred. The salts of the present invention include for example, salts of alkali metals (e.g., potassium, sodium, lithium, etc.), salts of alkaline earth metals (e.g., calcium, magnesium, etc.), ammonium salts (e.g., tetramethylammonium salt, tetrabutylammonium salt, etc.), pharmaceutical acceptable salts of organic amine (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts (salts of inorganic acids (e.g., hydrochloride, hydrobromide, hydroiodide, sulfate, phosphate, nitrate etc.), and salts of organic acids (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.).

The compound of the present invention can be made to N-oxide by a voluntary method. N-oxide means nitrogen atom of the compound represented by formula (I) is oxidized.

The compound represented by formula (I), a salt thereof, or an N-oxide thereof or a salt thereof can be also converted into a solvate. The solvate preferably includes non-toxic, soluble ones. A solvate of the present invention includes the solvate of, such as, water, alcohol solvent (e.g., methanol, ethanol etc.) and so on.

[Cyclodextrin Clathrate Compound]

The compounds of the present invention represented by formula (I), a salt thereof, an N-oxide thereof or a solvate thereof, or a prodrug thereof may be converted into the corresponding cyclodextrin clathrates by the method described in the specification of JP-B-50-3362, 52-31404 or 61-52146 using α-, β- or γ-cyclodextrin or a mixture thereof. Converting into the corresponding cyclodextrin clathrates serves to increase the stability and solubility in water of the compounds, and therefore it is useful in the use for pharmaceuticals.

[Prodrug]

The prodrug of the compounds of the present invention means a compound is converted into the compound represented by formula (I) by reaction with enzymes, gastric acids and so on within an organism. The prodrug of the compound of the present invention include, when the compounds represented by formula (I) have amino, the prodrug is the compound the amino of which is acylated, alkylated, phosphorylated or borated (e.g., the compound is that the amino of the compound of present invention is eicosanoated, alanylated, pentylaminocarbonylated, (5-methyl-2-oxo-1,3-dioxolan-4-yl)methoxycarbonylated, tetrahydrofuranated, pyrrolidylmethylated, pivaloyloxymethylated, acetoxymethylated, tert-butylated, etc.); when the compound of the present invention has hydroxy, the prodrug is the compound the hydroxy of which is acylated, alkylated, phosphorylated or borated (e.g., the compound is that the hydroxy of the compound of the present invention is acetylated, palmitoylated, propanoylated, pivaloylated, succinylated, fumarylated, alanylated, dimethylaminomethylcarbonylated etc.); when the compound of the present invention has carboxy, the prodrug is the compound the carboxyl of which is esterified or amidated (e.g., the compound is that the carboxy of the compound of the present invention is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated etc.); and so on. These compounds can be prepared by known methods. In addition, the prodrug of the compound of the present invention may be either hydrate or non-hydrate. In addition, the prodrug of the compound of the present invention may be converted into the compound of the present invention under the physiological condition which is described in "the development of medicine" vol. 7 "molecular design" published in 1991 Hirokawa shoten p.p. 163-198.

Further, the compound represented by formula (I) may be labeled with isotopes (e.g. $^3H$, $^{14}C$, $^{35}S$, $^{125}I$ etc.) and so on.

The compound in the present invention represented by formula (I), a salt thereof, an N-oxide thereof, or a solvate thereof, or a prodrug thereof or a cyclodextrin clathrate (hereinafter collectively abbreviated to the compound in the present invention) is the compound which has superior solubility, absorbability and metabolic stability, and sustains pharmacological activity ($EP_4$ agonistic activity) for a long time, additionally, has weak inhibitory activity of drug-metabolizing enzyme and lower toxicity, such as actions on circulatory organs and so on. These properties are most important physical, chemical, pharmaceutical properties which are required in case of development of pharmaceutical products. The compound in the present invention meets these conditions and has a possibility to be great pharmaceutical products. [refer to The Merck Manual of Diagnosis and Therapy (17th Ed.), Merck & Co.]

It can be evaluated that the compound in the present invention is useful for pharmaceutical product by the methods described in the following various experimental systems, biological examples and the methods which can be properly improved them to practice. In addition, it can be easily evaluated that the compound in the present invention is superior pharmacokinetically in respect of, such as, length of serum half-life, stability in gastrointestinal tract, oral absorbability, bioavailability etc., by the known method, such as, the methods described in "Drug bioavailability (Science of evaluation and improvement)", Gendai-Iryo, published in 1998 Jul. 6 and so on.

[Processes for the Preparation of the Compound in the Present Invention]

The compound in the present invention can be prepared by known methods, such as, the methods described in WO03/009872, WO00/003980, EP855389, EP985663, WO00/015608, WO01/149661, WO01/166518, PCT/JP2004/000419 (WO2004/065365), WO01/24647, WO02/042268, WO03/008377, WO03/035064, WO03/053923, WO03/103664, WO03/007941, US2005/0049227, WO04/085430, WO04/085431 or WO04/063158, or the pursuant methods thereof.

[Toxicity]

Toxicity of the compound in the present invention is very low, and it is safe enough to use as a pharmaceutical agent.

[Application to Pharmaceutical Products]

$EP_4$ agonist is useful as a preventive and/or treatment agent for lower urinary tract diseases, in particular, cystitis or urethritis. Since $EP_4$ agonist is useful as a preventive and/or treatment agent for lower urinary tract diseases, it is useful in ameliorating symptoms of lower urinary tract diseases such as (1) pollakiuria, (2) urgency of urination, (3) pain in the reproductive organs and/or lower urinary tract (for example, bladder pain, urinary tract pain, vulvar pain, vaginal pain, scrotal pain, perineal pain, pelvic pain, etc.) and/or (4) discomfort in the reproductive organs and/or lower urinary tract.

In addition, $EP_4$ agonist is useful since it improves bladder capacity and/or bladder compliance, protects and/or promotes the regeneration of bladder mucosa and/or bladder epithelial cells.

$EP_4$ agonist which is a preventive and/or treatment agent for lower urinary tract diseases of the present invention may be administered in combination with other medicaments to accomplish the following purposes:

1) To compensate for and/or enhance treatment effect of lower urinary tract diseases;

2) To improve the kinetics/absorption of the compound to be combined and reduce the dose of said $EP_4$ agonist of the present invention; and/or 3) To eliminate the side effect of said $EP_4$ agonist of the present invention to be combined $EP_4$ agonist of the present invention and other medicaments may be administered in the form of formulation having these components incorporated in one preparation or may be administered in separate preparations. In the case where these medicaments are administered in separate preparations, they may be administered simultaneously or at different times. In the latter case, $EP_4$ agonist of the present invention may be administered before the other medicaments. Alternatively, the other medicaments may be administered before $EP_4$ agonist of the present invention. The method for the administration of these may be the same or different.

The other medicaments may be low-molecular compounds. In addition, they may be macromolecular protein, polypeptide, polynucleotide (DNA, RNA, and gene), antisense, decoy, antibody or vaccine and so on. The dose of the other medicaments can be accordingly selected as a standard of clinical dose. Additionally, the compounding ratio of $EP_4$ agonist of the present invention and the other medicaments can be accordingly selected by the age and body weight of administering object, the administration method, the administration time, the object disease, the symptom, the combination etc. For example, the other medicaments may be used from 0.01 to 100 parts by weight relative to 1 part by weight of $EP_4$ agonist of the present invention. The other medicaments may be administered combining at appropriate ratio. The other medicaments to compensate for and/or enhance the preventive and/or treatment effect of lower urinary tract diseases do not only include ones which have ever been found but ones which will be found from now based on the below-mentioned mechanism.

The other medicaments include, for example, heparin preparation, dimethylsulfoxide preparation, hyaluronic acid preparation, resiniferatoxin preparation, botulinum toxin preparation, pentosan polysulfate sodium, antidepressant, antibiotics, analgesic/anti-inflammatory agent, antispasmodic agent, anti-histaminic agent, anti-allergic agent, the other curative for urinary tract disease (for example, anticholinergic drugs, $\alpha_1$ agonist, $\alpha_1$ antagonist, GABA agonist, antidiuretic, antiandrogen, progestational hormone, $NK_1$ antagonist, $\beta_3$ agonist, P2X antagonist, potassium channel opener, LPA, capsaicin (resiniferatoxin), muscarine (M1, M3) antagonist, 5-HT reuptake inhibitor, $5-HT_{1A}$ antagonist, ACh antagonist, Ca channel antagonist, $EP_1$ antagonist, $EP_3$ antagonist).

Examples of antidepressant include tricyclic antidepressant (for example, imipramine hydrochloride, desipramine hydrochloride, clomipramine hydrochloride, trimipramine maleate, amitriptyline hydrochloride, nortriptyline hydrochloride, lofepramine hydrochloride, amoxapine, dosulepin hydrochloride etc.), tetracyclic antidepressant (for example, maprotiline, mianserin etc.) and the like.

Examples of anbiotics include cefuroxime sodium, meropenem trihydrate, netilmicin sulfate, sisomycin sulfate, ceftibuten, PA-1806, IB-367, tobramycin, PA-1420, doxorubicin, astromicin sulfate, cefetamet pivoxil hydrochloride and the like. Examples of inhalantion antibiotics include PA-1806, IB-367, tobramycin, PA-1420, doxorubicin, astromicin sulfate, cefetamet pivoxil hydrochloride and the like.

Examples of antispasmodic agent include carbamazepine, phenyloin, ethotoin, mephobarbital, metharbital, primidone, trimethadione, acetylpheneturide, ethosuximide, sodium valproate, acetazolamide, clonazepam, zonisamide, diazepam and the like.

Examples of analgesic/anti-inflammatory agent include ergotamine preparation (for example, dihydroergotamine mesilate, ergotamine tartrate etc.), opioid receptor agonist (for example, morphine sulfate, morphine hydrochloride, pethidine hydrochloride, fentanyl, pentazocine, buprenorpine hydrochloride etc.), steroids, nonsteroidal anti-inflammatory drug and the like.

Examples of steroids include external steroid such as clobetasol propionate, diflorasone diacetate, fluocinonide, mometasone furoate, betamethasone dipropionate, betamethasone butyrate propionate, betamethasone valerate, difluprednate, butesonid, diflucortolone valerate, amcinonide, halcinonide, dexamethasone, dexamethasone propionate, dexamethasone valerate, dexamethasone acetate, hydrocortisone acetate, hydrocortisone acetate, hydrocortisone butyrate propionate, deprodone propionate, prednisolone valerate acetate, fluocinolone acetonide, beclometasone dipropionate, triamcinolone acetonide, flumetasone pivalate, alclometasone dipropionate, clobetasone butyrate, prednisolone, beclometasone dipropionate and fludroxycortide etc., internal or injectable steroid such as cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethason acetate and betamethasone etc., inhalant steroid such as beclometasone dipropionate, fluticasone propionate, budesonide, flunisolide, triamcinolone, ST-126P, ciclesonide, dexamethasone, mometasone furoate, prasterone sulfonate, deflazacort, methylprednisolone suleptanate and methylprednisolone sodium succinate and the like.

Examples of nonsteroidal anti-inflammatory drug include sasapyrine, sodium salicylate, aspirin, combination of aspirin and dialuminate, diflunisal, indometacin, suprofen, ufenamate, dimethyl isopropylazulene, bufexamac, felbinac, diclofenac, tolmetin sodium, Clinoril, fenbufen, nabumetone, proglumetacin, indometacin farnesil, acemetacin, proglumetacin maleate, amfenac sodium, mofezolac, etodolac, ibuprofen, ibuprofen piconol, naproxen, flurbiprofen, flurbiprofenaxetil, ketoprofen, fenoprofen calcium, tiaprofen, oxaprozin, pranoprofen, loxoprofen sodium, alminoprofen, zaltoprofen, mefenamic acid, mefenamic acid aluminium, tolfenamic acid, floctafenine, ketophenylbutazon, oxyphenbutasone, piroxicam, tenoxicam, ampiroxicam, napageln ointment, epirizole, tiaramide hydrochloride, tinoridine hydrochloride, emorfazone, sulpyrine, migrenin, Saridon, Sedes G, Amipylo-N, Solvon, pyrine compounding cold medicine, acetaminophen, phenacetin, dimetotiazine mesilate, simetride-combined drug, non-pyrine-combined cold medicine and the like.

Examples of anti-histaminic agent include ketotifen fumarate, mequitazine, azelastine hydrochloride, oxatomide, terfenadine, emedastine difumarate, epinastine hydrochloride, astemizole, ebastine, cetirizine hydrochloride, bepotastine, fexofenadinehydrochloride, loratadine, desloratadine, olopatadine hydrochloride, TAK-427, ZCR-2060, NIP-530, mometasone furoate, mizolastine, BP-294, andolast, auranofin, acrivastine and the like.

Examples of anti-allergic agent include allergen extract, amlexanox, azelastine hydrochloride, bepotastinebesilate, cetirizine hydrochloride, ebastine, emedastine difumarate, epinastine hydrochloride, fexofenadine hydrochloride, ibudilast, ketotifen fumarate, loratadine, montelukast sodium, olopatadine hydrochloride, oxatomide, ozagrel hydrochloride, pemirolast potassium, pranlukast hydrate, ramatroban, repirinast, seratrodast, sodium cromoglicate, suplatast tosilate, tazanolast, tranilast, zafirlukast and the like.

Examples of anticholinergic drugs include oxybutynin hydrochloride, bethanechol chloride, propiverine hydrochloride, propantheline bromide, methylbenactyzium bromide, scopolamine butylbromide, tolterodine tartrate, trospium chloride, Z-338, K-112166-04, ONO-8025, darifenacin, YM-905 and the like.

Examples of muscarine antagonist include YM905, ONO-8025 and the like.

Examples of $\alpha_1$ agonist include midodrine hydrochloride and the like.

Examples of $\alpha_1$ antagonist include terazosin hydrochloride, bunazosin hydrochloride, urapidil, tamsulosin hydrochloride, doxazosin mesilate, prazosin hydrochloride, indolamine, naftopidil, alfzosin hydrochloride, AIO-8507L and the like.

Examples of GABA agonist include most minor tranquilizer, baclofen, midazolam and the like.

Examples of diuretic include mannitol, furosemide, acetazolamide, dichlorphenamide, methazolamide, trichlormethiazide, mefruside, spironolactone, aminophylline and the like.

Examples of $EP_1$ antagonist include the compound described in WO98/27053, the compound described in EP878465, the compound described in WO02/72564 and the like.

Examples of $EP_3$ antagonist include the compound described in WO02/16311, the compound described in WO02/20462 and the like.

In order to use $EP_4$ agonist of the present invention or $EP_4$ agonist of the present invention in combination with the other medicaments, these are normally administered to the entire or local part of human body orally or parenterally.

The doses to be administered are differently determined depending upon, for example, age, body weight, symptom, the desired therapeutic effect, the route of administration, and the duration of the treatment etc. In the human adult, the doses per person are generally from 0.1 ng to 1000 mg, by oral administration, from one time to several times per day, and from 0.1 ng to 100 mg, by parenteral administration, from one time to several times per day, or continuous administration from 1 to 24 hours per day from vein.

As mentioned above, the doses vary depending upon various conditions. Therefore, there are cases in which doses lower than the above described doses are enough or more administration is necessary greater doses than the ranges specified above.

$EP_4$ agonist of the present invention, or concomitant medication combined $EP_4$ agonist of the present invention with other preparations may be administered in the composition of, for example, solid compositions or liquid compositions, each for oral administration, or injections, external use, suppositories, eye drops inhalant each for parenteral administration.

Examples of the solid preparations for internal use for oral administration include tablets, pills, capsules, powders, granules and the like. The capsules include hard capsules and soft capsules. The tablets include sublingual tablets, intraoral patches, orally fast disintegrating tablets and the like.

Such a solid preparation for internal use is prepared by a formulation method commonly employed by using one or two or more active substances either as it is or as a mixture with an excipient (lactose, mannitol, glucose, microcrystalline cellulose, starch, etc.), a binder (hydroxypropylcellulose, polyvinylpyrrolidone, magnesium metasilicate aluminate, etc.), a disintegrating agent (calcium cellulose glycolate, etc.), a lubricant (magnesium stearate, etc.), a stabilizer and a dissolution aid (glutamic acid, aspartic acid, etc.). If necessary, it may be coated with a coating agent (sucrose, gelatin, hydroxypropylcellulose, hydroxypropylmethylcellulose phthalate, etc.). It may be coated with two or more layers. Moreover, capsules made of an absorbable material such as gelatin are involved in the scope thereof.

The sublingual tablets may be prepared in accordance with a well known method. For example, a sublingual tablet is prepared by a formulation method commonly employed by using one or more active substances mixed with an excipient (lactose, mannitol, glucose, microcrystalline cellulose, colloidal silica, starch, etc.), a binder (hydroxypropylcellulose, polyvinylpyrrolidone, magnesium metasilicate aluminate, etc.), a disintegrator (starch, L-hydroxypropyl cellulose, carboxymethyl cellulose, croscarmellose sodium, calcium cellulose glycolate, etc.), a lubricant (magnesium stearate, etc.), a swelling agent (hydroxypropyl cellulose, hydroxylpropylmethy cellulose, carbopol, carboxymethyl cellulose, polyvinyl alcohol, xanthan gum, guar gum, etc.), a swelling aid agent (glucose, fructose, mannitol, xylitol, erythritol, maltose, trehalose, phosphate, citrate, silicate, glycine, glutamic acid, arginine, etc.), a stabilizer, a dissolution aid (polyethylene glycol, propylene glycol, glutamic acid, aspartic acid, etc.), a flavoring agent (orange, strawberry, mint, lemon, vanilla, etc.). If necessary, it may be coated with a coating agent (sucrose, gelatin, hydroxypropylcellulose, hydroxypropylmethylcellulose phthalate, etc.). If necessary, it may be coated with two or more layers. Moreover, it may also further comprise some additives such as antiseptics, antioxidants, coloring agents, sweetening agents and the like. The intraoral patch may be prepared in accordance with a well known method. For example, a intraoral patch is prepared by a formulation method commonly employed by using one or more active substances mixed with an excipient (lactose, mannitol, glucose, microcrystalline cellulose, colloidal silica, starch, etc.), a binder (hydroxypropylcellulose, polyvinylpyrrolidone, magnesium metasilicate aluminate, etc.), a disintegrator (starch, L-hydroxypropyl cellulose, carboxymethyl cellulose, croscarmellose sodium, calcium cellulose glycolate, etc.), a lubricant (magnesium stearate, etc.), a attach agent (hydroxypropyl cellulose, hydroxylpropylmethy cellulose, carbopol, carboxymethyl cellulose, polyvinyl alcohol, xanthan gum, guar gum, etc.), a attach aid agent (glucose, fructose, mannitol, xylitol, erythritol, maltose, trehalose, phosphate, citrate, silicate, glycine, glutamic acid, arginine, etc.), a stabilizer, a dissolution aid (polyethylene glycol, propylene glycol, glutamic acid, aspartic acid, etc.), a flavoring agent (orange, strawberry, mint, lemon, vanilla, etc.) and the like. If necessary, it may be coated with a coating agent (sucrose, gelatin, hydroxypropylcellulose, hydroxypropylmethylcellulose phthalate, etc.) and the like. If necessary, it may be coated with two or more layers. Moreover, it may also further comprise some additives such as antiseptics, antioxidants, coloring agents, sweetening agents and the like.

The orally fast disintegrating tablet may be prepared in accordance with a well known method. For example, a orally fast disintegrating tablet is prepared by a formulation method commonly employed by using one or more active substances directly, or active substances by covering with adequate coating agent (ethylcellulose, hydroxypropylcellulose, hydroxypropylmethylcellulose, acrylic acid and methacrylic acid copolymer etc.), plasticizer (polyethylenegrycol, triethyl citrate etc.) to bulks or granulating bulk particles mixed with an excipient (lactose, mannitol, glucose, microcrystalline cellulose, colloidal silica, starch, etc.), a binder (hydroxypropylcellulose, polyvinylpyrrolidone, magnesium metasilicate aluminate, etc.), a disintegrator (starch, L-hydroxypropyl cellulose, carboxymethyl cellulose, croscarmellose sodium, calcium cellulose glycolate, etc.), a lubricant (magnesium stearate, etc.), a dispersion aid agent (glucose, fructose, mannitol, xylitol, erythritol, maltose, trehalose, phosphate, citrate, silicate, grylcine, glutamate, arginine etc.), a stabilizer and a dissolution aid (polyethylene glycol, propylene glycol, glutamic acid, aspartic acid, etc.), a flavoring agent (orange, strawberry, mint, lemon, vanilla, etc.) and the like. If necessary, it may be coated with a coating agent (sucrose, gelatin, hydroxypropylcellulose, hydroxypropylmethylcellulose phthalate, etc.) and the like. If necessary, it may be coated with two or more layers. Moreover, it may also further comprise some additives such as antiseptics, antioxidants, coloring agents, sweetening agents and the like.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

In the parenteral administration, formulation of external use include, for example, ointment, gel, cream, poultice, patch, liniment, atomized agent, inhalation, spray, aerosol and nasal spray, etc. They includes one or more of the active compound(s) and be prepared by known method or usual method.

Ointment is prepared by known method or usual method. For example, it is prepared by levigation or fusion of one or more of the active compound(s) and substrate. The substrate of ointment is selected from known or usual one. For example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), wax (yellow beeswax, spermaceti, ceresin, etc.), surfactant (polyoxyethylene alkyl ether phosphoric acid ester, etc.), higher alcohol (cetanol, stearil alcohol, cetostearyl alcohol, etc.), silicon oil (dimethyl polysiloxane, etc.), hydrocarbon (hydrophilic petrolatum, white petrolatum, purified lanolin, liquid paraffin, etc.), glycol (ethylene glycol, diethylene glycol, propylene glycol, polyethylene glycol, macrogol, etc.), vegetable oil (castor oil, olive oil, sesame oil, turpentine oil, etc.), animal oil (mink oil, egg yolk oil, squalane, squalene, etc.), water, absorption accelerator, skin fit inhibitor, etc. are used as single substance selected from them or mixture which consists of two or more kinds that is selected from them. Moreover, humectant, preservative agent, stabilizer, antioxidative agent, fragrant materials, etc. may be contained.

Gel is prepared by known method or usual method. For example, it is prepared by fusion of one or more of the active compound(s) and substrate. The substrate of gel is selected from known or usual one. For example, lower alcohol (ethanol, isopropylalcohol, etc.), gelling agent (carboxy methyl cellulose, hydroxy ethyl cellulose, hydroxy propyl cellulose, ethyl cellulose, etc.), neutralizing agent, (triethanolamine, diisopropanolamine, etc.), surfactant, (polyethylene glycol monostearate, etc.), gum, water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Cream is prepared by known method or usual method. For example, it is prepared by fusion or emulsification of one or more of the active compound(s) and substrate. The substrate of cream is selected from known or usual one. For example, higher fatty acid ester, lower alcohol, hydrocarbon, polyalcohol (propylene glycol, 1,3-butylene glycol, etc.), higher alcohol (2-hexyldecanol, cetanol, etc.), emulsifying agent (polyoxyethylene alkyl ether, fatty acid ester, etc.), water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Poultice is prepared by known method or usual method. For example, it is prepared by fusion of one or more of the active compound(s) and substrate, and then the kneaded one is laid over support medium. The substrate for poultice is selected from known or usual one. For example, thickening agent (polyacrylic acid, polyvinylpyrolidone, gum acacia, starch, gelatin, methyl cellulose, etc.), a wetting agent (urea, glycerin, propylenegrycol etc.), bulking agent (kaolin, zinc oxide, talc, calcium, magnesium, etc.), water, solubilizing agent, thickener, skin fit inhibitor, etc. are used as single substance selected from them or mixture which consists of two or more kinds that is selected from them. Moreover, preservative agent, antioxidative agent, fragrant materials, etc. may be contained.

Patch is prepared by known method or usual method. For example, it is prepared by fusion of one or more of the active compound(s) and substrate, and then laid over support medium. The substrate for patch is selected from known or usual one. For example, polymer substrate, fat, higher fatty acid, thickener, skin fit inhibitor, etc. are used as single substance selected from them or mixture which consists of two or more kinds that is selected from them. Moreover, preservative agent, antioxidative agent, fragrant materials, etc. may be contained.

Liniment is prepared by known method or usual method. For example, one or more of the active compound(s) may be dissolved, suspended or emulsified in water, alcohol (ethanol, polyethylene glycol, etc.), higher fatty acid, glycerin, soap, emulsifying agent, suspending agent, etc. as single substance selected from them or mixture which consists of two or more kinds that is selected from them. Moreover, preservative agent, antioxidative agent, fragrant materials, etc. may be contained.

Atomized agent, inhalation and spray may comprise in addition to a diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355.

The dosage of inhalations for parenreral administration include aerosol, powders for inhalation or liquids for inhalation. The liquids for inhalation may be dissolved or suspended in water or the other appropriate solvent as needed.

Such inhalations are prepared in a known method.

For example, a liquid for inhalation is prepared by selecting proper additives from an antiseptic (benzalkonium chloride or p-aminobenzonic acid), a coloring agent, a buffering agent (sodium phosphate or sodium acetate), an isotonizing agent (sodium chloride or concentrated glycerin), thickening agent (carboxyvinylpolymer), or an accelerator of absorption, etc., if necessary.

A powder for inhalation is prepared by selecting proper additives from a lubricant agent (such as stearin acid and the salt thereof), a binding agent, (such as starch, dextrin), a diluting agent (such as lactose, cellulose), a coloring agent, an antiseptic (such as benzalkonium chloride or p-aminobenzonic acid), an accelerator of absorption, etc., if necessary.

In case of administration of liquid for inhalation, spray (atomizer, nebulizer) is usually used and in case of administration of powder for inhalation, inhalation administration apparatus for powder agents is usually used.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (glutamic acid, aspartic acid, POLYSORBATE80 (registered trade mark) etc.), suspending agents, emulsifying agents, soothing agent, buffering agents, preservative. They may be sterilized at a final step, or may be prepared by an aseptic manipulation. They may also be manufactured in the form of sterile solid forms, for example, freeze-dried products, which may be dissolved in sterile water or some other sterile diluent(s) for injection immediately before use.

The other compositions for parenteral administration include suppositories for intrarectal administration and pessaries for vaginal administration which comprise one or more of the active substance(s) and may be prepared by methods known per se.

In addition, in case of administration to treat cystitis, the above-described injections can be also injected into bladder.

EFFECT OF THE INVENTION $EP_4$ agonist is useful as a preventive and/or treatment agent for lower urinary tract diseases. In particularly, it is useful as a preventive and/or treatment agent for cystitis and/or urethritis. Because $EP_4$ agonist is useful as a preventive and/or treatment agent for lower urinary tract diseases, $EP_4$ agonist is useful in ameliorating symptoms of lower urinary tract diseases such as (1) pollakiuria, (2) urgency of urination, (3) pain in the reproductive organs and/or lower urinary tract (for example, bladder pain, urinary tract pain, vulvar pain, vaginal pain, scrotal pain, perineal pain, pelvic pain, etc.) and/or (4) discomfort in the reproductive organs and/or lower urinary tract. Since the intravesical injection of $EP_1$ agonist and $EP_3$ agonist induces stimulation of bladder, a selective $EP_4$ agonist is useful as a preventive and/or treatment agent for lower urinary tract diseases having no side effect.

In addition, $EP_4$ agonist is useful as an agent for improving bladder capacity and/or bladder compliance.

Moreover, $EP_4$ agonist is useful as an agent for protecting bladder mucosa and/or bladder epithelial cells and/or promoting the regeneration thereof

BEST MODE FOR CARRYING OUT THE INVENTION

An effect of the present invention by $EP_4$ agonist is established by the following experiments. However, that the present invention is not limited thereto.

Biological Example

Example 1

Effect in the Model of Cyclophosphamide-Induced Cystitis (1) Catheter Indwelling Female Wistar rats (around 9 weeks old) were anesthetized with sodium pentobarbital (40 mg/kg, i.p.). After median incision of the hypogastrium, the top of bladder was incised. A catheter for use in cystometry was filled with physiological saline and then was inserted through the top hole into bladder. The other end of the catheter was fixed subcutaneously in the dorsal part. 0.1 mL Vicillin S500 (Meiji Seika Kaisha, Ltd.; 100 mg titers/mL distilled water/rat) was injected into the buttock muscle. Then, the rats were fed for 6 days or more, and subsequently subjected to the following treatment.

(2) The Making of the Model of Cyclophosphamide-Induced Cystitis and the Administration of the Test Compounds The model of cyclophosphamide-induced cystitis was prepared by a single dose intraperitoneal administration of cyclophosphamide (Sigma; 150 mg/kg). Distilled water is administered intraperitoneally for the control group.

The test compound of each dose was administrated orally 30 minutes before the treatment of cyclophosphamide, and 4, 20, 30 and 45 hours after the treatment of cyclophosphamide. The solvent group (hereinafter, it may be referred to as vehicle.) was administrated distilled water which is the solvent of the test compound. The following cystometry was carried out 48 hours after the treatment of cyclophosphamide.

(3) Cystometry

The rats anesthetized with diethyl ether were kept in ballman cage. The tip of the indwelling catheter for use in measurement of voiding pressure was connected through a three-way valve. Another end of the three-way valve was connected to a pressure transducer, while the other end was connected to a syringe for intravesical injection which was mounted on an infusion pump. A signal of voiding pressure was recorded using an amp recorder of strain pressure After awaking from anesthesia, saline was injected into the bladder of the rats at a rate of 2.85 mL/h. After the pattern of the micturition reflex was stable, the residual urine was removed. Afterwards, saline was injected again into the bladder at a rate of 2.85 mL/h, and the voiding pressure and the urination interval were measured. The bladder capacity was calculated from the urination interval. The bladder compliance was calculated by dividing the bladder capacity by the voiding pressure.

[Result]

Figure 1:
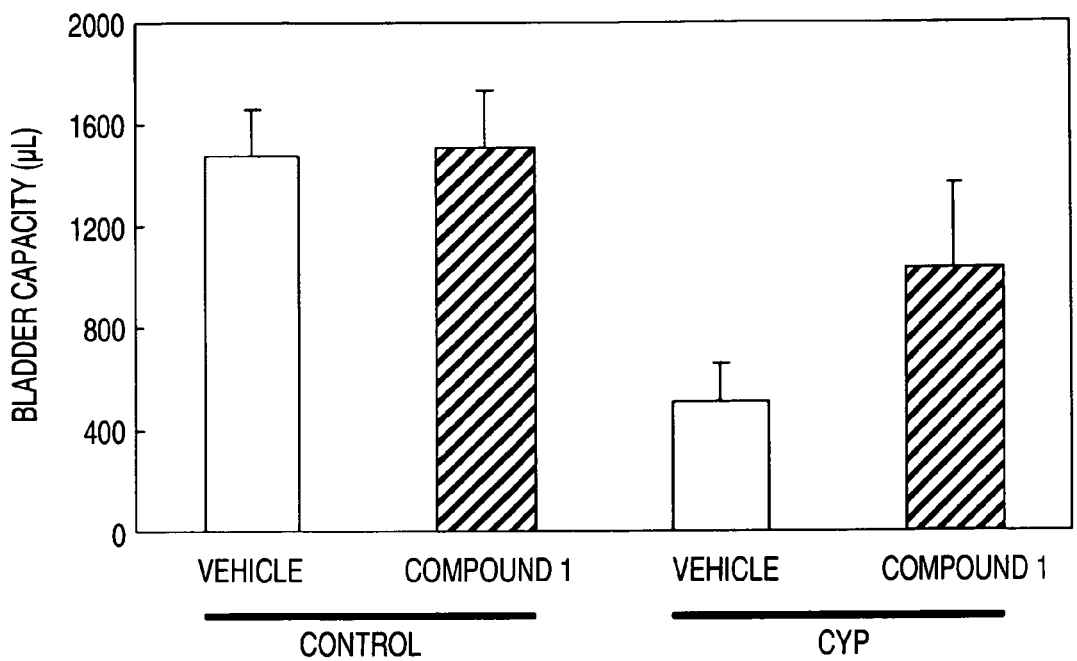
FIG. 1 is the graph which shows an effect of compound 1 (4-[(2-{(2R)-2-[(1E,3S)-4-(4-fluorophenyl)-3-hydroxybut-1-enyl]-5-oxopyrrolidin-1-yl}ethyl)sulfanyl]butanoic acid) for bladder capacity in the model of cyclophosphamide-induced cystitis in rats.

The bladder capacity decreased by the treatment of cyclophosphamide and the capacity became about ¼ of Control that was not treated by cyclophosphamide (FIG. 1).

Figure 2:
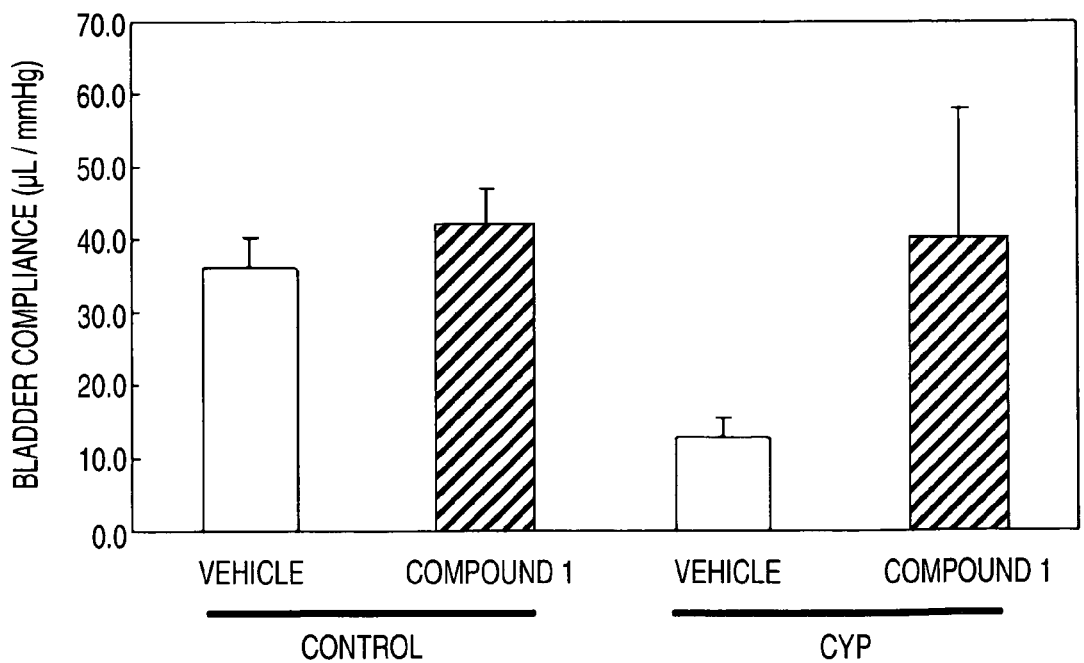
FIG. 2 is the graph which shows an effect of compound 1 for bladder compliance in the model of cyclophosphamide-induced cystitis in rats.

The bladder compliance which shows the progress of the bladder decreased remarkably by the same treatment, too (FIG. 2).

The decrease of the bladder capacity induced by cyclophosphamide and the decrease of the bladder compliance were improved by administering 300 μg/kg orally of 4-[(2-{(2R)-2-[(1E,3S)-4-(4-fluorophenyl)-3-hydroxybut-1-enyl]-5-oxopyrrolidin-1-yl}ethyl)sulfanyl]butanoic acid (hereinafter abbreviated to compound 1.) which is EP4 agonist as test compound (FIG. 1, FIG. 2).

Figure 3:
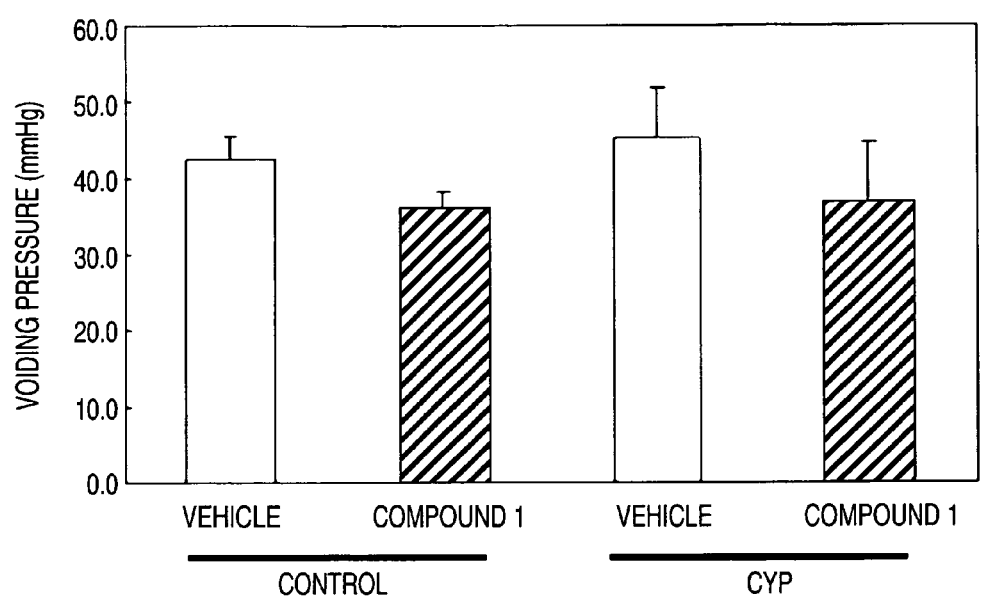
FIG. 3 is the graph which shows an effect of compound 1 for voiding pressure in the model of cyclophosphamide-induced cystitis in rats.

Regardless of the presence of the cyclophosphamide treatment, the voiding pressure was decreased by the administration of compound 1 (FIG. 3).

Moreover, the decrease of the bladder capacity and the bladder compliance induced by cyclophosphamide was improved by administering orally 1000 μg/kg of methyl 4-{[2-((1R,2R,3R)-3-hydroxy-2-{(1E,3S)-3-hydroxy-4-[3-(methoxymethyl)phenyl]but-1-enyl}-5-oxocyclopenty)ethyl]sulfanyl}butanoate α-cyclodextrin clathrate (hereinafter abbreviated to compound 2.) which is EP$_4$ agonist.

Formulation Example 1

Tablet

A solution (100 ml) of 4-[(2-{(2R)-2-[(1E,3S)-4-(4-fluorophenyl)-3-hydroxybut-1-enyl]-5-oxopyrrolidine-1-yl}ethyl)sulfanyl]butanoic acid (30 mg) in ethanol, magnesium stearate (1000 mg), silicon dioxide (200 mg), talc (100 mg), and carboxymethylcellulose calcium (2000 mg) were admixed by conventional method, dried, then micro crystalline cellulose (50.0 g) was added into the mixture and the total volume was adjusted to 100 g. They were sufficiently admixed until they were equalized, and then punched out by conventional method to obtain 1000 tablets each containing 30 pg of active ingredient.

Formulation Example 2

Injection

α-Cyclodextrin clathrate compound (60 mg) of 4-[(2-{(2R)-2-[(1E,3S)-4-(4-fluorophenyl)-3-hydroxybut-1-enyl]-5-oxopyrrolidine-1-yl}ethyl)sulfanyl]butanoic acid (5 mg) was dissolved into distilled water for injection (3000 ml), the solution was aseptically filtrated with membrane filter and then the solution 3 ml each was filled into a 5 ml capacity ampoule for injection to obtain injections (1000 ampoules) containing 5 μg of active ingredient.

INDUSTRIAL APPLICABILITY

EP$_4$ agonist is useful in the following as pharmaceutical product. EP$_4$ agonist is useful as a preventive and/or treatment agent for lower urinary tract diseases, in particular, cystitis and/or urethritis. Moreover, since EP$_4$ agonist is useful as a preventive and/or treatment agent for lower urinary tract diseases, it is useful in ameliorating symptoms of lower urinary tract diseases such as (1) pollakiuria, (2) urgency of urination, (3) pain in the reproductive organs and/or lower urinary tract (for example, bladder pain, urinary tract pain, vulvar pain, vaginal pain, scrotal pain, perineal pain, pelvic pain, etc.) and/or (4) discomfort in the reproductive organs and/or lower urinary tract.

In addition, EP$_4$ agonist is useful as an agent for improving bladder capacity and/or bladder compliance.

Moreover, EP$_4$ agonist is useful as an agent for protecting bladder mucosa and/or bladder epithelial cells and/or promoting the regeneration thereof.

The invention claimed is:

1. A method for improving bladder compliance and/or bladder capacity in a patient having interstitial cystitis, which comprises administering an effective amount of a compound selected from the group consisting of:
   4-{[2-(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and
   methyl 4-{[2-(1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate,
   a salt thereof or a cyclodextrin clathrate thereof, to a patient or subject in need thereof.

* * * * *